(12) United States Patent
Abudawoud et al.

(10) Patent No.: US 10,723,631 B2
(45) Date of Patent: Jul. 28, 2020

(54) METHODS OF PRODUCING COMPOSITE ZEOLITE CATALYSTS FOR HEAVY REFORMATE CONVERSION INTO XYLENES

(71) Applicants: Saudi Arabian Oil Company, Dhahran (SA); Universitat Politecnica De Valencia, Valencia (ES); Consejo Superior De Investigaciones Cientificas, Madrid (ES)

(72) Inventors: Raed Hasan Abudawoud, Al-Khobar (SA); Avelino Corma Canos, Valencia (ES); M. Teresa Portilla Ovejero, Valencia (ES); Vicente J. Margarit Benavent, Valencia (ES); M. Teresa Navarro Villalba, Valencia (ES); M. Cristina Martinez Sanchez, Valencia (ES); Ibrahim M. Al-Zahrani, Dammam (SA)

(73) Assignees: Saudi Arabian Oil Company, Dhahran (SA); Universitat Politecnica De Valencia, Valencia (ES); Consejo Superior De Investigaciones Cientificas, Madrid (ES)

( * ) Notice: Subject to any disclaimer, the term of this patent is extended or adjusted under 35 U.S.C. 154(b) by 0 days.

(21) Appl. No.: 16/299,704

(22) Filed: Mar. 12, 2019

(65) Prior Publication Data
US 2019/0284057 A1    Sep. 19, 2019

(30) Foreign Application Priority Data
Mar. 14, 2018 (EP) .................................. 18382172

(51) Int. Cl.
*C01B 39/02*     (2006.01)
*C07C 15/08*     (2006.01)
(Continued)

(52) U.S. Cl.
CPC ............... *C01B 39/04* (2013.01); *B01J 29/18* (2013.01); *B01J 29/22* (2013.01); *B01J 29/24* (2013.01);
(Continued)

(58) Field of Classification Search
CPC ..... C01B 39/023; C01B 39/40; C01B 39/265; C01P 2002/72; C07C 15/08;
(Continued)

(56) References Cited

U.S. PATENT DOCUMENTS

| 4,467,129 A | 8/1984 | Iwayama et al. |
| 4,963,337 A | 10/1990 | Zones |

(Continued)

FOREIGN PATENT DOCUMENTS

| CN | 101121132 A | 2/2008 |
| CN | 101121137 A | 2/2008 |

(Continued)

OTHER PUBLICATIONS

International Search Report and Written Opinion dated Jun. 27, 2019 pertaining to International application No. PCT/US2019/021592 filed Mar. 11, 2019, 15 pgs.

(Continued)

*Primary Examiner* — David M Brunsman
(74) *Attorney, Agent, or Firm* — Dinsmore & Shohl LLP

(57) ABSTRACT

A method of forming composite zeolite catalyst particles includes combining a silicon source, an aqueous organic structure directing agent having a polyquaternary ammonium compound, water and an aluminum source to form a catalyst gel. The method also includes heating the catalyst gel to form the composite zeolite catalyst particle having an intergrowth region with a mixture of both Mordenite crystals and ZSM-5 crystals. An associated method of making xylene includes feeding heavy reformate to a reactor, the (Continued)

reactor containing the composite zeolite catalyst particles, and producing xylene by simultaneously performing dealkylation and transalkylation of the heavy reformate in the reactor, where each composite zeolite catalyst particle is able to catalyze both the dealkylation and transalkylation reactions.

15 Claims, 18 Drawing Sheets

(51) Int. Cl.
| | |
|---|---|
| B01J 29/80 | (2006.01) |
| C01B 39/04 | (2006.01) |
| B01J 29/26 | (2006.01) |
| B01J 29/48 | (2006.01) |
| B01J 37/02 | (2006.01) |
| B01J 37/04 | (2006.01) |
| B01J 37/08 | (2006.01) |
| C01B 39/26 | (2006.01) |
| C01B 39/38 | (2006.01) |
| C07C 4/18 | (2006.01) |
| C07C 6/12 | (2006.01) |
| B01J 29/22 | (2006.01) |
| B01J 29/18 | (2006.01) |
| B01J 35/00 | (2006.01) |
| B01J 29/46 | (2006.01) |
| B01J 29/24 | (2006.01) |
| B01J 29/44 | (2006.01) |
| B01J 29/40 | (2006.01) |
| C01B 39/40 | (2006.01) |
| B01J 29/06 | (2006.01) |

(52) U.S. Cl.
CPC .............. *B01J 29/26* (2013.01); *B01J 29/40* (2013.01); *B01J 29/44* (2013.01); *B01J 29/46* (2013.01); *B01J 29/48* (2013.01); *B01J 29/80* (2013.01); *B01J 35/002* (2013.01); *B01J 37/0201* (2013.01); *B01J 37/04* (2013.01); *B01J 37/08* (2013.01); *C01B 39/023* (2013.01); *C01B 39/26* (2013.01); *C01B 39/265* (2013.01); *C01B 39/38* (2013.01); *C01B 39/40* (2013.01); *C07C 4/18* (2013.01); *C07C 6/12* (2013.01); *C07C 6/126* (2013.01); *B01J 2029/062* (2013.01); *B01J 2229/62* (2013.01); *C01P 2002/01* (2013.01); *C01P 2002/72* (2013.01); *C01P 2002/82* (2013.01); *C07C 15/08* (2013.01); *C07C 2529/18* (2013.01); *C07C 2529/22* (2013.01); *C07C 2529/24* (2013.01); *C07C 2529/26* (2013.01); *C07C 2529/40* (2013.01); *C07C 2529/44* (2013.01); *C07C 2529/46* (2013.01); *C07C 2529/48* (2013.01); *C07C 2529/80* (2013.01)

(58) Field of Classification Search
CPC ....... C07C 2529/80; B01J 29/18; B01J 29/22; B01J 29/26; B01J 29/40; B01J 29/44; B01J 29/48; B01J 29/80; B01J 2029/062
See application file for complete search history.

(56) References Cited

U.S. PATENT DOCUMENTS

| | | |
|---|---|---|
| 5,043,513 A | 8/1991 | Howley et al. |
| 5,120,425 A | 6/1992 | Zones et al. |
| 5,865,986 A | 2/1999 | Buchanan et al. |
| 5,942,651 A | 8/1999 | Beech, Jr. et al. |
| 5,952,536 A | 9/1999 | Nacamuli et al. |
| 7,393,989 B2 | 7/2008 | Negiz et al. |
| 8,242,321 B2 | 8/2012 | Boldingh et al. |
| 8,329,973 B2 | 12/2012 | Inui et al. |
| 8,653,315 B2 | 2/2014 | Ali |
| 9,242,236 B2 * | 1/2016 | Xie ..................... B01J 29/80 |
| 2002/0092797 A1 | 7/2002 | Choi et al. |
| 2005/0234279 A1 | 10/2005 | Serra et al. |
| 2009/0023968 A1 | 1/2009 | Wang et al. |
| 2009/0112034 A1 | 4/2009 | Levin |
| 2009/0325785 A1 | 12/2009 | Moscoso et al. |
| 2010/0029467 A1 | 2/2010 | Inui |
| 2011/0127193 A1 | 6/2011 | Xie et al. |
| 2012/0083635 A1 | 4/2012 | Boldingh et al. |
| 2012/0165558 A1 | 6/2012 | Ryoo et al. |
| 2012/0258852 A1 | 10/2012 | Martinez et al. |
| 2013/0261365 A1 | 10/2013 | Wang et al. |
| 2013/0281750 A1 | 10/2013 | Abudawoud |
| 2018/0134637 A1* | 5/2018 | Lai ...................... B01J 37/0215 |

FOREIGN PATENT DOCUMENTS

| | | | |
|---|---|---|---|
| CN | 101190418 A | * | 6/2008 |
| CN | 101190418 A | | 6/2008 |
| CN | 101190864 A | | 6/2008 |
| CN | 101191069 A | | 6/2008 |
| CN | 101347746 A | * | 1/2009 |
| CN | 101348407 A | * | 1/2009 |
| CN | 101602639 A | * | 12/2009 |
| CN | 101885663 A | | 11/2010 |
| CN | 101811063 B | | 10/2012 |
| CN | 104437611 A | | 3/2015 |
| CN | 104437613 A | | 3/2015 |
| EP | 042754 A1 | | 6/1981 |
| EP | 109962 A1 | | 6/1984 |
| EP | 1586376 A1 | | 10/2005 |
| EP | 1775277 A1 | | 4/2007 |
| WO | 2004046278 A1 | | 6/2004 |
| WO | 2005118515 A1 | | 12/2005 |
| WO | 2010150996 A2 | | 12/2010 |
| WO | 2018011122 A1 | | 1/2018 |
| WO | 2018071184 A1 | | 4/2018 |
| WO | 2018231340 A1 | | 12/2018 |

OTHER PUBLICATIONS

International Search Report and Written Opinion dated Jun. 28, 2019 pertaining to International application No. PCT/US2019/021597 filed Mar. 11, 2019, 17 pgs.

International Search Report and Written Opinion dated Jun. 26, 2019 pertaining to International application No. PCT/US2019/021590 filed Mar. 11, 2019, 23 pgs.

International Search Report and Written Opinion dated Jun. 26, 2019 pertaining to International application No. PCT/US2019/021595 filed Mar. 11, 2019, 20 pgs.

Ali et al., "Selective production of xylenes from alkyl-aromatics and heavy reformates over dual-zeolite catalyst", Catalysis Today, vol. 243, pp. 118-127 (2015).

Al-Khattaf et al., "Catalytic transformation of methyl benzenes over zeolite catalysts", Applied Catalysis A: General 394, pp. 176-190, 2011.

Calderia et al., "Properties of hierarchical Beta zeolites prepared from protozeolitic nanounits for the catalytic cracking of high density polyethylene", Applied Catalysts A: General 531, pp. 187-196, 2017.

Choi et al., "Stable single-unit-cell nanosheets of zeolite MFI as active and long-lived catalysts", Nature, vol. 461, pp. 246-250, Sep. 10, 2009.

Corma et al., "Discovery of new paraffin isomerization catalysts based on SO4 2-/ZrO2 and Wox/ZrO2 applying combinatorial techniques", Catalysts Today 81, pp. 495-506, 2003.

Han et al., Zeolite Synthesis Using Flexible Diquartemary Alkylammonium Ions $(C_nH_{2n+1})2HN+(CH2)5N+H(C_nH_{2n+1})2$ with n=1-5 as Structure-Directing Agents, Chem Mater, vol. 17, pp. 477-486, 2005.

(56) References Cited

OTHER PUBLICATIONS

Jackowski et al., "Diquaternary Ammonium Compounds in Zeolite Synthesis: Cyclic and Polycyclic N-Heterocycles Connected by Methylene Chains", American Chemical Society, 131, 1092-1100 (2009).

Jo et al., "Capping with Multivalent Surfactants for Zeolite Nanocrystal Synthesis", Angew. Chem, vol. 125, pp. 10198-10201, 2013 with Supporting Information.

Kim et al., "Bulk crystal seeing on generation of mesoporoes by organosilane surfactants in zeolite synthesis", Electronic Supplementary (ESI) for Journal of Masterials Chemistry A., The Royal Society of Chemistry 2014.

Kong et al., "Fabrication of core/shell structure via overgrowth of ZSM-5 layers on mordenite cyrstals", Microporous and Mesoporous Materials, vol. 119, pp. 91-96, 2009.

Konysheva et al., "Effect of Nature of Heteroelement (Ba, Ga, Al) on Adsorption of Acid Characteristics of Hierarchical Porous Zeolites of MOR, BEA and MTW Strucural Types", Theoretical and Experimental Chemistry, vol. 53, No. 6, pp. 410-416, Jan. 2018.

Va Laak et al., "Mesoporous mordenites obtained by sequential acid and alkaline treatments—Catalysts for cumene production with enhanced accessibility", Journal of Catalysis, vol. 276, pp. 170-180, 2010.

Lee et al., "Reinvestigation into the synthesis of zeolites using diquaternary alkylammonium ions (CH3)3N+(CH2)nN+f(CH3)3 with n=3-10 as structure-directing agents", Microporous and Mesoporous Materials, vol. 68, pp. 97-104, 2004.

Lee et al., "Zeolite synthesis in the presence of flexible diquaternary alkylammonium ions (C2H5)3N+(CH2)nN+(C2H5)3 with n+3-10 as structure-directing agents", Microporous and Mesoporous Materials, vol. 60, pp. 237-249, 2003.

Li et al., "One-pot synthesis of hierarchical mordenite and its performance in the benzylation of benzene with benzyl alcohol", J. Matter Sci, vol. 50, pp. 5059-5067, 2015.

Mihayli et al., "Transformation of ethylbenzene-m-xylene misture on zeolites with different structures", J. Porous Matter, vol. 21, pp. 485-493, 2014.

Liu et al., "Catalytic Properties of Hierarchical Mordenite Nanosheets Synthesized by Self-Assembly Between Subnanocrystals and Organic Templates", Catal Lett, vol. 146, pp. 249-254, 2016 with Electronic Supplementary Information.

Moller et al., "Mesoporosity—a new dimension for Zeolites", Chem Soc Rev. vol. 42, pp. 3689-3707, 2013.

Ordomsky et al., "Cumene disproportionation over micro/mesoprous catalysts obtained by recrystallization of mordenite", Journal of Catalysis, vol. 295, pp. 207-216, 2012.

Shvets et al., "New Approaches to Creation of Micro- and Mesoporous Functional Materials", Theoretical and Experimental Chemiustry, vol. 53, No. 5, Nov. 2017.

Thommes et al., "Physisorption of gases, with special reference to the evaluation of surface area and pore size distribution (IUPAC Technical Report)", Pure Appl. Chem., 87(9-10), pp. 1051-1069, 2015.

Verboekend et al., "Design of hierarchical zeolite catalysts by desilication", Catalysis Science & Technology, vol. 1, pp. 879-890, 2011.

Vitvarova et al., "Catalytic applications and FTIR investigation of zeolite SSZ-33 after isomorphous substitution", Microporous and Mesoporous Materials, vol. 194, pp. 174-182, 2014.

Zones et al., "Boron-beta zeolite hydrothermal conversions: the influence of template structure and of boron concentration and source", Microporous Materials, vol. 2, pp. 543-555, 1994.

European Search Report pertaining to European Application No. 18382172.7 dated Jan. 4, 2019.

European Search Report pertaining to European Application No. 18382170.1 dated Sep. 27, 2018.

European Search Report pertaining to European Application No. 18382168.5 dated Sep. 27, 2018.

European Search Report pertaining to European Application No. 18382167.7 dated Jan. 4, 2019.

European Search Report pertaining to European Application No. 18382169.3 dated Sep. 27, 2018.

European Search Report pertaining to European Application No. 18382171.9 dated Oct. 5, 2018.

Galarneau et al., Validity of the t-plot Method to Assess Microporosity in Hierarchical Micro/Mesoporous Materials, Langmuir 2014, 9 pgs.

Office Action dated Dec. 2, 2019 pertaining to U.S. Appl. No. 16/299,717, filed Mar. 12, 2019, 26 pgs.

Office Action dated Dec. 4, 2019 pertaining to U.S. Appl. No. 16/299,723, filed Mar. 12, 2019, 30 pgs.

Office Action dated Dec. 20, 2019 pertaining to U.S. Appl. No. 16/299,838, filed Mar. 12, 2019, 30 pgs.

Office Action dated Dec. 20, 2019 pertaining to U.S. Appl. No. 16/299,844, filed Mar. 12, 2019, 31 pgs.

Machine translation CN 101811063, Aug. 25, 2010, retrieved Dec. 6, 2019 (Year: 2019).

Camblor et al. "Characterization of Nanocrystalline Zeolite Beta" Microporous and Mesoporous Materials 25 (1998) pp. 59-74 (Year: 1998).

International Search Report and Written Opinion dated Sep. 20, 2019 pertaining to International application No. PCT/US2019/021594 filed Mar. 11, 2019.

Notice of Allowance and Fee(s) Due dated Apr. 17, 2020 pertaining to U.S. Appl. No. 16/299,832, filed Mar. 12, 2019, 31 pgs.

* cited by examiner

METHODS OF PRODUCING COMPOSITE ZEOLITE CATALYSTS FOR HEAVY REFORMATE CONVERSION INTO XYLENES

CROSS REFERENCE TO RELATED APPLICATIONS

This application claims priority to European Application No. 18382172.7, filed Mar. 14, 2018 which is hereby incorporated by reference in its entirety.

TECHNICAL FIELD

Embodiments of the present specification generally relate to catalysts, and specifically relate to forming composite zeolite catalysts and methods of using for heavy reformate conversion.

BACKGROUND

Heavy reformate (HR), containing mainly $C_{9+}$ aromatics, is the fraction that remains after extraction of the more valuable BTEX (benzene, toluene, ethylbenzene, xylene) fraction from the catalytic reformate or the pyrolysis gasoline. Traditionally this fraction was directly added to the gasoline pool. However, due to the restriction of the benzene content in gasoline by environmental regulations, it is important to find alternative ways of upgrading this stream into other valuable products. One option is to convert the heavy aromatics in the heavy reformate into xylenes. Demand is growing faster for xylene derivatives than for benzene derivatives. Therefore, a higher yield of xylenes at the expense of benzene yield is a favorable objective. Heavy reformate may be converted into xylenes and other compounds by means of dealkylation of the $C_{9+}$ alkylaromatics or by transalkylation of these compounds with benzene or toluene.

Heavy reformate may also be converted into xylenes by dealkylation of the $C_{9+}$ alkylaromatics to benzene and toluene, and further transalkylation of these compounds formed by dealkylation with other $C_{9+}$ alkylaromatics present in the feed. Regardless, these means to produce xylenes by simultaneous dealkylation and transalkylation have limited efficiency, because of the sequential nature of the conversion reaction process where products of a first reaction are utilized in a second reaction.

SUMMARY

Accordingly, ongoing needs exist for catalysts suitable for efficiently converting heavy reformates to produce xylenes. Embodiments of the present disclosure are related to composite zeolite catalyst particles, their preparation methods and performance, particularly to the synthesis of such catalyst particles having intimate contact at the nanocrystal level between the zeolite constituents. The zeolite composite catalysts may convert a mixture of heavy aromatic compounds (such as those present in heavy reformate), particularly $C_{9+}$ aromatic hydrocarbons to benzene, toluene, and xylenes, and particularly to commercially valuable xylenes.

According to one embodiment, a method of forming composite zeolite catalyst particles is provided. The method includes combining a silicon source, an organic structure directing agent, water, and an aluminum source to form a catalyst gel. The organic structure directing agent includes a polyquaternary ammonium compound. Finally, the method includes heating the catalyst gel to form the composite zeolite catalyst particles. The composite zeolite catalyst particle includes both Mordenite and ZSM-5 zeolites and is characterized by having an intergrowth region with a mixture of both Mordenite crystals and ZSM-5 crystals.

According to another embodiment, a composite zeolite catalyst is provided. The composite zeolite catalyst comprises ZSM-5 and Mordenite within a single catalyst particle. Further, the composite zeolite catalyst has an intergrowth region with a mixture of Mordenite crystals and ZSM-5 crystals, the intergrowth of ZSM-5 and Mordenite characterized by an XRD curve having signature peaks at: 6.6±0.2, 7.9±0.2, 8.8±0.2, 9.8±0.2, 13.6±0.2, 19.7±0.2, 22.5±0.2, 23.1±0.2, 23.9±0.2, 25.8±0.2, 26.4±0.2, 27.7±0.2.

According to yet another embodiment, a method of making xylene is provided. The method includes feeding heavy reformate to a reactor. The reactor contains a composite zeolite catalyst including a plurality of catalyst particles. Each catalyst particle includes both ZSM-5 and Mordenite zeolites, and has an intergrowth region with a mixture of both Mordenite crystals and ZSM-5 crystals. Further, the method includes producing xylene by performing transalkylation and dealkylation of the heavy reformate in the reactor, where each catalyst particle is able to simultaneously catalyze both the transalkylation and dealkylation reactions.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Reference will now be made in detail to embodiments of a method of forming a composite zeolite catalyst and conversion of heavy reformate with the composite zeolite catalyst.

The main components of heavy reformate are ethyl-toluenes (methyl-ethyl-benzenes, MEB) and trimethyl-benzenes (TMB). The structures of the MEB isomers and TMB isomers are provided infra.

These aromatics can be converted into the more valuable BTEX compounds by means of dealkylation of the $C_{9+}$ alkylaromatics, or by transalkylation of these compounds with benzene or toluene. The aim of the process is to maximize the production of xylenes by de-ethylation of MEB and transalkylation of TMB. Specifically, transalkylation of TMB present in the feed with the toluene formed as a product of de-ethylation of MEB.

The dealkylation of MEB to toluene and ethane is provided infra. Dealkylation of MEB in the presence of a Brønsted acid catalyst initially produces toluene and ethylene. However, the ethylene may be subsequently hydrogenated to ethane in the presence of an adequate hydrogenation catalyst. If the hydrogenation functionality is not effective, portions of the ethylene may not be hydrogenated to ethane and as such may be present in the product gases, or it may be converted to oligomers or other products.

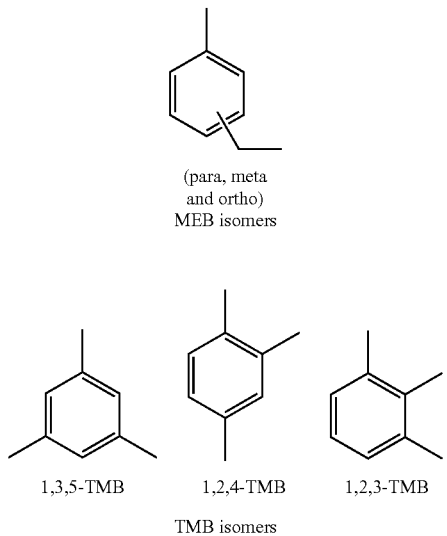

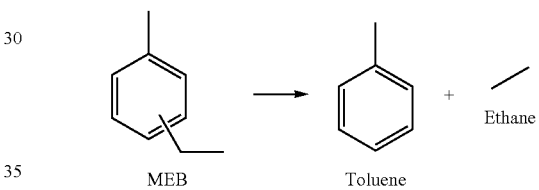

The transalkylation of TMB present in the heavy reformate with the toluene formed from dealkylation of MEB to toluene and ethane is provided infra.

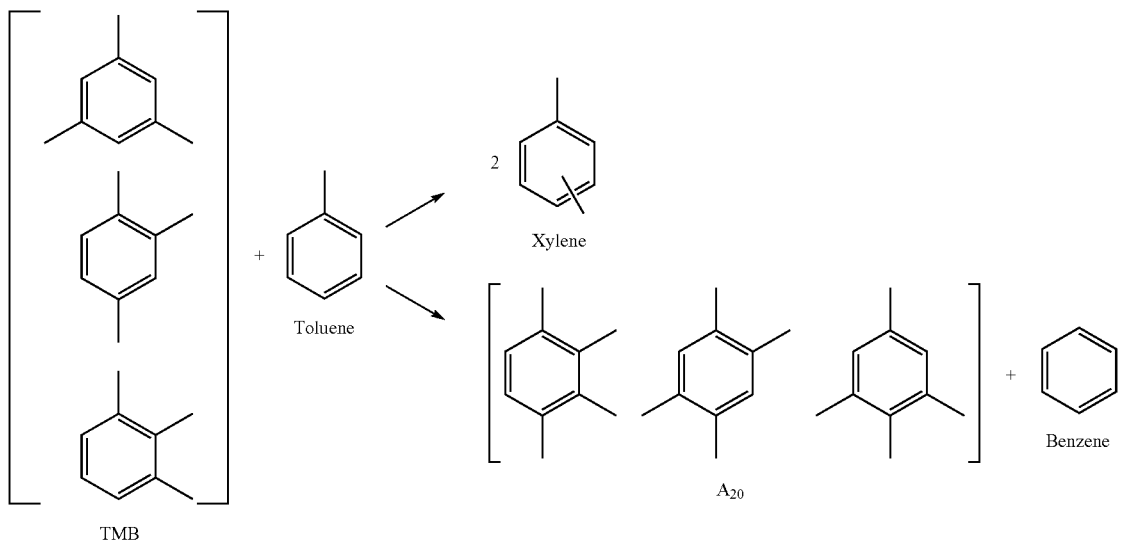

Additionally, toluene and TMB may also undergo a disproportionation reaction leading to xylenes and benzene or xylenes and tetramethylbenzenes ($A_{10}$), respectively. The chemical reactions are provided infra.

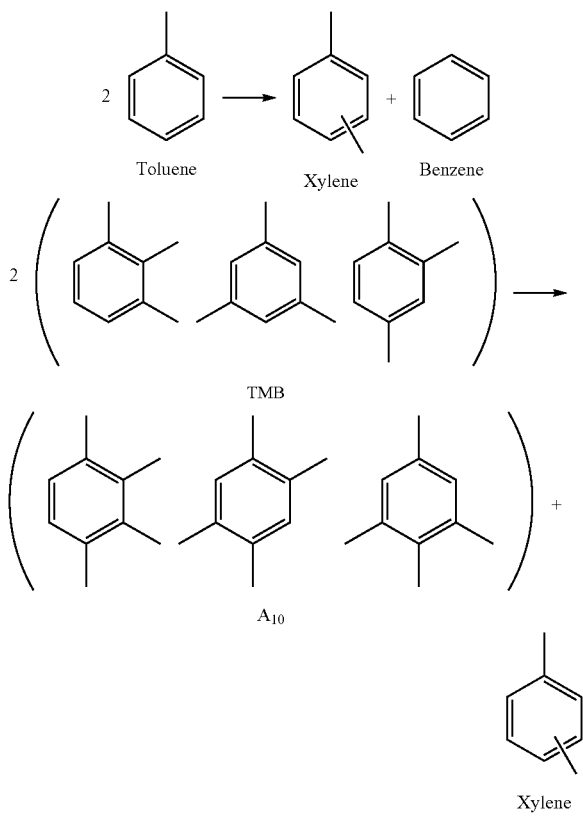

The method of forming composite zeolite catalyst particles includes combining NaOH, water, a silicon source, an organic structure directing agent, and an aluminum source in a reagent container to form a catalyst gel. The catalyst gel is stirred for homogenization, and then heated in a sealed vessel under autogenous pressure to form the composite zeolite catalyst particles. The formed composite zeolite catalyst particles are a bulk catalyst without an underlying support matrix.

The composite zeolite catalyst in one or more embodiments comprises Mordenite and ZSM-5. ZSM-5 is an aluminosilicate zeolite of the pentasil family of zeolites. ZSM-5 (Zeolite Socony Mobil-5) has a Mordenite Framework Inverted (MFI) framework with an ordered crystal structure presenting 10-ring pores. Mordenite, an aluminosilicate, has a MOR framework with parallel 12-ring and 8-ring pores interconnected by 8-ring pores.

Figure 2:
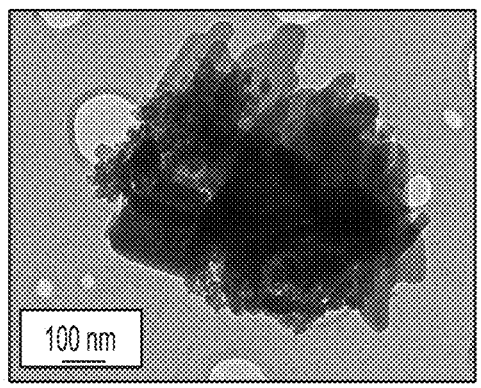
FIG. 2 is a Transmission Electron Microscopy (TEM) micrograph of a composite zeolite catalyst with a Mordenite to ZSM-5 ratio of 75:25 synthesized in accordance with one or more embodiments of the present disclosure.
Figure 3:
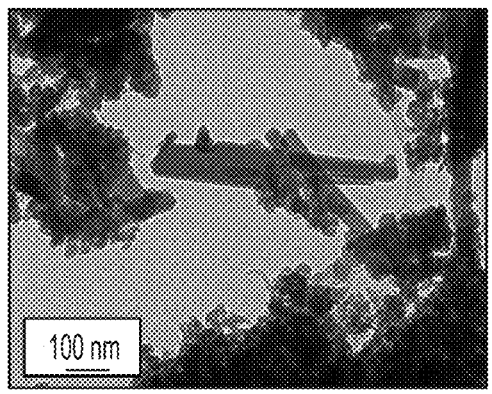
FIG. 3 is a TEM micrograph of a composite zeolite catalyst with a Mordenite to ZSM-5 ratio of 40:60 synthesized in accordance with one or more embodiments of the present disclosure.

The simultaneous crystallization of both ZSM-5 and Mordenite from the catalyst gel generates a final composite zeolite catalyst particle with both Mordenite and ZSM-5 in intimate contact at the nanometer scale. As used in this disclosure, "intimate contact" means the Mordenite and ZSM-5 are intermixed within a single particle of the composite zeolite catalysts such that crystals of ZSM-5 and crystals of Mordenite are abutting when viewed at a nanoscale level. The ZSM-5 and Mordenite crystals are dispersed throughout the composite zeolite catalyst particle and form an intimate mixture of both ZSM-5 and Mordenite crystals interwoven within each composite zeolite catalyst particle. With reference to FIGS. 2 and 3, both ZSM-5 and Mordenite crystals interwoven within each composite zeolite catalyst particle may be observed. FIG. 2 provides a TEM image of the composite zeolite catalyst particles with a molar ratio of Mordenite to ZSM-5 of approximately 3:1 (75% Mordenite and 25% ZSM-5). Similarly, FIG. 3 provides a TEM image of the composite zeolite catalyst particles with a molar ratio of Mordenite to ZSM-5 of approximately 2:3 (40% Mordenite and 60% ZSM-5). The area of interwoven ZSM-5 and Mordenite crystals is termed the intergrowth region. The intergrowth region includes distinct crystals of ZSM-5 and Mordenite, but their simultaneous formation results in the crystals of each type in intimate contact at the nanometer scale.

With reference to FIGS. 2 and 3, the crystals of ZSM-5 and Mordenite appear as distinct crystals. Structurally, the samples of the disclosed composite zeolite catalysts are intimate mixtures of Mordenite and ZSM-5 zeolite crystals obtained by a one-pot synthesis procedure, but the TEM images presented in FIGS. 2 and 3 show that the two zeolites, ZSM-5 and Mordenite, crystallize in individual and distinct crystallites. The morphology of the two zeolites is different with ZSM-5 crystalizing as nanocrystals and mordenite being present as nanorods or nanolayers. The TEM images also show that these crystals are very small and in intimate contact at the nanometer scale.

Without wishing to be bound by theory, it is believed the intimate mixing of the ZSM-5 and Mordenite crystals enhances the consecutive dealkylation-transalkylation reactions desired for conversion of the industrial heavy reformate into xylenes by reducing the transport distance of reaction products between zeolite types. In this way, the composite zeolite catalyst allows one-pot dealkylation of the MEB in heavy reformate and transalkylation of the TMB with the in-situ produced toluene to achieve maximum xylenes selectivity and catalyst performance.

The synthesis method for the composite zeolite catalyst particles achieves improved performance in conversion of heavy reformate as compared to monozeolitic based catalysts or as compared to multizeolitic based catalyst prepared by physical mixtures of the individual zeolite components. This improvement is even more profound when carrying out the transalkylation of a heavy reformate in the absence of added toluene or benzene, because these two aromatics must be produced in-situ from $C_{9+}$ aromatics such as with dealkylation of MEB contained within the feed. The intimate contact of the Mordenite and ZSM-5 in the composite zeolite catalyst produced in accordance with this disclosure allows the toluene produced from dealkylation of MEB to be more readily available for use in the transalkylation reaction of TMB or disproportionation reaction of toluene for the ultimate production of xylenes.

In one or more embodiments, the silicon source is a silica gel. The silica gel may be a 20 to 60 weight percent (wt. %) suspension of silica in water, a 25 to 55 wt. % suspension of silica in water, a 30 to 50 wt. % suspension of silica in water, or a 35 to 45 wt. % suspension of silica in water. The silicon source may also be silicon oxide, silicon halide, tetraalkyl orthosilicate, silicic acid, fumed silica, sodium silicate, colloidal silica, a previously synthesized crystalline material comprising silicon, a previously synthesized amorphous material comprising silicon, and combinations thereof. For example, the silicon source may be Ludox AS-40 (W.R. Grace & Co.—Conn.), which is a 40 wt. % suspension of colloidal silica in water. According to manufacturer specifications, the particle size of Ludox AS-40 is 20-24 nm.

The organic structure directing agent may comprise one or more polyquaternary ammonium compounds. In various embodiments, the polyquaternary ammonium compound may comprise a diquaternary ammonium compound, a triquaternary ammonium compound, a tetraquaternary ammonium compound, or a pentaquaternary ammonium compound. In embodiments, the polyquaternary ammonium compound comprises a structure in accordance with the following formula [1].

Formula [1]

In embodiments, X in formula [1] is a hydroxide group (OH) or a halogen selected from Cl, Br, I, or combinations thereof. In embodiments, R1 in formula [1] is a $C_{8-22}$ alkyl group, $C_{12-22}$ alkyl group, or $C_{18-22}$ alkyl group which may be substituted or unsubstituted. In embodiments, R2 in formula [1] is a $C_{3-6}$ alkyl group, $C_{4-6}$ alkyl group, or $C_{5-6}$ alkyl group which may be substituted or unsubstituted. In embodiments, R3 in formula [1] is a $C_{1-8}$ alkyl group, $C_{4-8}$ alkyl group, or $C_{6-8}$ alkyl group which may be substituted or unsubstituted. In the present disclosure, the organic structure directing agent may be expressed in a general form as: the number of carbon atoms of R1—the number of carbon atoms of R2—the number of carbon atoms of R3 (for example, $C_{22-6-6}$: an organic structure directing agent having 22 carbon atoms in R1, 6 carbon atoms in R2, 6 carbon atoms in R3, and 2 ammonium functional groups, $C_{22-6-6-6}$: an organic surfactant having 22 carbon atoms in R1, 6 carbon atoms in R2, 6 carbon atoms m R3, 6 carbon atoms in R4, and 3 ammonium functional groups). Additionally, the substituent X may be specified as Cl, Br, I, or OH following the general expression (for example, $C_{22-6-6}Br_2$: an organic structure directing agent having 22 carbon atoms in R1, 6 carbon atoms in R2, 6 carbon atoms in R3, 2 ammonium functional groups, and the substituent X being Br; $C_{22-6-6-6}(OH)_3$, an organic surfactant having 22 carbon atoms in R1, 6 carbon atoms in R2, 6 carbon atoms in R3, 6 carbon atoms in R4, and 3 ammonium functional groups, and the substituent X being a hydroxide).

In one embodiment, the organic structure directing agent may be $C_{22-6-6}Br_2$ which is a solid compound, and is not in aqueous solution. In one embodiment, the organic structure directing agent may be in aqueous solution and utilize $C_{22-6-6}(OH)_2$. In embodiments, the aqueous solution of the organic structure directing agent comprises between 5 and 15 wt. % polyquaternary ammonium cations and between 85 and 95 wt. % water. In various further embodiments, the aqueous organic structure directing agent comprises between 8 and 13 wt. % polyquaternary ammonium cations and between 87 and 92 wt. % water, or the aqueous organic structure directing agent comprises between 9 and 12 wt. % polyquaternary ammonium cations and between 88 and 91 wt. % water.

The organic structure directing agent directs the synthesis process towards crystallization of the desired species. For this disclosure, the organic structure directing agent directs the synthesis towards crystallization of nanocrystals of both ZSM-5 and Mordenite in different proportion that will depend on the composition of the synthesis gel.

In one or more embodiments, the aluminum precursor is a sodium aluminate ($NaAlO_2$), alumina ($Al_2O_3$), aluminum isopropoxide ($Al(O-i-Pr)_3$), aluminum hydroxide ($Al(OH)_3$), aluminum oxide hydroxide ($AlO(OH)$) (also called boehmite), or combinations thereof. Other compositions are also contemplated for the aluminum precursor. As an example, commercially available $NaAlO_2$ may be supplied by Carlo Erba Reagents (Val-de-Reuil, France). The composition of $NaAlO_2$ supplied by Carlo Erba Reagents is specified as 53-55 wt. % $Al_2O_3$ and 47-45 wt. % $Na_2O$. In embodiments, $NaAlO_2$ is formed from 47 wt. % $Al_2O_3$, 34.4 wt. % $Na_2O$ and 18.6 wt. % $H_2O$.

The catalyst gel is formed by combining the silicon source, the organic structure directing agent, and the aluminum precursor and water, so the water content matches the one given in the gel compositions provided infra in Table 1. In one or more embodiments, the aluminum source is added in combination with NaOH. From the dissolved silicon source, new species form which will react with each other and with the aluminum species in solution to form the crystalline zeolite structure. The silicon source, the organic structure directing agent, and the aluminum precursor are stirred continuously to ensure homogenization of the formed catalyst gel. If homogenization is not achieved crystallization of other silica or alumina phases may compete with the desired ZSM-5 and Mordenite. Mixing of the components is performed at room temperature, and once the gel is homogenized it is heated in an autoclave or other suitable heating equipment for crystallization of the zeolites.

The composition of the catalyst gel varies depending on the desired ZSM-5 and Mordenite ratio of the final composite zeolite catalyst particle. In one embodiment, formation of 75 wt. % Mordenite and 25 wt. % ZSM-5 may utilize a catalyst gel composition having molar ratios of 0.20 $Na_2O$:1 $SiO_2$:0.05 $Al_2O_3$:0.075 polyquaternary ammonium compound:40$H_2O$. In another embodiment, formation of 40 wt. % Mordenite and 60 wt. % ZSM-5 may utilize a catalyst gel composition of 0.30 $Na_2O$:1 $SiO_2$: 0.025 $Al_2O_3$: 0.075 polyquaternary ammonium compound: 40$H_2O$. In another embodiment, it will be appreciated that other ratios such as 80 wt. % Mordenite and 20 wt. % ZSM-5 or 20 wt. % Mordenite and 80 wt. % ZSM-5 may be achieved by adjusting the ratios of the silicon source, the aluminum precursor, and the aqueous organic structure directing agent in the ultimate catalyst gel accordingly.

Subsequently, in one or more embodiments, the catalyst gel is heated in a sealed vessel under autogenous pressure in combination with stirring. Autogenous pressure is the pressure naturally produced by heating within a closed and sealed vessel. In one or more embodiments, the catalyst gel is introduced into an oven heated to between 130° C. and 180° C. In addition to placement in a heated oven, other heating methods such as introduction to a heated autoclave or coverage with a heating jacket are also contemplated as suitable. In various further embodiments, the catalyst gel is introduced into the sealed vessel heated to between 135° C. and 170° C. 140° C. and 160° C., or approximately 150° C. Additionally, in various embodiments, the heating of the catalyst gel in the sealed vessel is maintained with stirring for 4 to 18 days, 5 to 17 days, 10 to 16 days, or approximately 14 days. Additionally, stirring of the catalyst gel during heating in the sealed vessel under autogenous pressure may be maintained at approximately 10 to 100 rotations per minute (rpm), 20 to 90 rpm, 30 to 80 rpm, 40 to 75 rpm, 50 to 70 rpm, or 55 to 65 rpm for the entirety or only a portion of the heating cycle. It is envisioned that stirring speed may vary over the course of the heating cycle, such as with a speed of approximately 60 rpm for a first period and approximately 20 rpm for a second period.

In at least one embodiment, the catalyst gel is heated in a vessel allowing for a continuous process. In one or more embodiments, the catalyst gel is introduced into an oven, such as a tunnel oven, heated to between 130° C. and 180° C. In various further embodiments, the catalyst gel is introduced into the vessel heated to between 135° C. and 170° C., 140° C. and 160° C., or approximately 150° C.

In at least one embodiment, the resultant powder from heating the catalyst gel is washed with hot water and dried in an oven overnight. The hot water may be 40° C. to 80° C., 40° C. to 60° C., 45° C. to 55° C., greater than 40° C., greater than 50° C., or greater than 60° C. Additionally, the drying may be at 80° C. to 150° C., 80° C. to 120° C., 90° C. to 110° C., or approximately 100° C. for a duration of 8 to 16 hours (h), 8 to 12 h, 8 to 10 h, 10 to 16 h, 10 to 14 h. or 10 to 12 h.

The composite zeolite catalyst may further be calcined. In one or more embodiments, the composite zeolite catalyst is calcined at a temperature of 500° C. for 8 hours in air.

The specific catalyst gel compositions and the use of the organic structure directing agent are able to direct the synthesis process to the simultaneous crystallization of both Mordenite and ZSM-5. The organic structure directing agent allows for the crystallization of the ZSM-5 and Mordenite as intimate mixtures, with crystals in the nanometer range. The catalyst gel composition determines the proportion of ZSM-5 and Mordenite in the final solid.

The ratio of ZSM-5 and Mordenite within the composite zeolite catalyst may be determined with X-ray diffraction (XRD) analysis. The X-ray diffraction patterns for pure phase Mordenite and ZSM-5 are distinct with representative peaks. Identification of the distinct peaks representing ZSM-5 and Mordenite respectively in an X-ray diffraction pattern for a catalyst sample with each zeolite type present allows a determination of the proportion of each zeolite in the mixture. Example XRD patterns for pure phase Mordenite, pure phase ZSM-5, differing ratios of Mordenite and ZSM-5, as well as commercially available physical mixtures of Mordenite and ZSM-5 are provided in FIG. 1. The relative intensity of the differing peaks in an XRD pattern for the composite zeolite crystal particles allows the ratio of Mordenite and ZSM-5 to be determined and as such the disclosed ratios are approximated based on the XRD patterns of FIG. 1. Distinct peaks are observed for Mordenite at 6.6±0.2, 8.8±0.2, 9.8±0.2, 13.6±0.2, 19.7±0.2, 22.5±0.2, 25.8±0.2, 26.4±0.2, 27.7±0.2. (2θ degree) and are labeled with a triangle, and four distinct peaks in groupings of two are observable for ZSM-5 at 7.9, 8.8, 23.1 and 23.9 (2θ degree) and are labeled with a star. The XRD patterns for 75:25 Mordenite:ZSM-5 and 40:60 Mordenite:ZSM-5 include varying relative intensity of each of the peaks as the ratio of Mordenite to ZSM-5 varies.

The Mordenite and ZSM-5 components of the composite zeolite catalyst particles are formed in intimate contact at the nanocrystal level. For purposes of this disclosure, crystals with sizes below 0.1 microns are considered nanocrystals. The ZSM-5 and Mordenite are present as individual crystals with their own respective unique morphology. The ZSM-5 crystallizes as nanocrystals, whereas Mordenite crystallizes as nanorods, nanolayers, or a combination of nanorods and nanolayers. With reference to FIG. 2 and FIG. 3, transmission electron microscopy (TEM) micrographs are provided of composite ZSM-5/Mordenite zeolite catalysts formed in accordance with the present disclosure. FIG. 2 illustrates the layered crystalline formations of the Mordenite along with the nanocrystal nature of the ZSM-5. Similarly, FIG. 3 illustrates primarily the nanocrystalline nature of the ZSM-5. The presence of a majority of nanocrystal (ZSM-5) is visible in FIG. 3 for a composite zeolite catalyst with a 40:60 weight ratio of Mordenite:ZSM-5. Similarly, the presence of a majority of layered crystal (Mordenite) is visible in FIG. 2 for a composite zeolite catalyst with a 75:25 weight ratio of Mordenite:ZSM-5.

Moreover, the zeolite composite catalyst particles may be impregnated with metals for catalysis, for example, metals such as molybdenum, chromium, platinum, nickel, tungsten, palladium, ruthenium, gold, rhenium, rhodium, or combinations thereof. In one embodiment, the impregnated metal is rhenium (Re). The metal component may exist within the final zeolite composite catalyst particle as a compound, such as an active metal oxide, an active metal sulfide or active metal halide, in chemical combination with one or more of the other ingredients of the composite, or as an elemental metal. The impregnated metal component may be present in the final composite zeolite catalyst particle in any amount that is catalytically effective, for example from 0.01 to 20.0 wt. %, or from 2 to 5 wt. %, or from 0.1 to 1.5 wt. %, or approximately 0.5 wt. % of the composite zeolite catalyst particle.

Metals are added to the catalyst for their hydrogenation functionality. The dealkylation, transalkylation and disproportionation reactions take place on the Brønsted acid sites of the composite zeolite catalysts. However, the hydrogenation function of the metal component is utilized to convert ethylene into ethane and may also enhance the desorption of coke precursors. The conversion of ethylene into ethane avoids the oligomerization of the olefin to products that may deactivate the catalyst.

In one or more embodiments, the metals are incorporated into the zeolite composite catalyst particles by ion exchange or impregnation of their salts in aqueous solution. The catalysts with the incorporated metals are then calcined in air and the metals are converted into their oxide forms, which do not present hydrogenation activity. In order to be active for hydrogenation these oxides are converted into metal sulfides, for example metal sulfides of Mo, Ni, or W, or the metal oxides can be reduced to their elemental metal form, for example elemental forms of Mo, Pt, Re, Pd, or Rh. In one or more embodiments, the composite zeolite catalyst particles are impregnated with rhenium in the form of ammonium perrhenate ($NH_4ReO_4$) through an incipient wetness procedure. In one or more embodiments, the composite zeolite catalyst particles are impregnated with molybdenum in the form of ammonium molybdate tetrahydrate (($NH_4)_6Mo_7O_{24}.4H_2O$) through an incipient wetness procedure.

In one embodiment, the molar ratio of silicon to aluminum (Si/Al) in the zeolite composite catalyst is from 5:1 to 30:1. Without wishing to be bound, pure mordenite is obtained with a Si/Al molar ratio of 6.5 and pure ZSM-5 is obtained with a Si/Al molar ratio of 26. In further embodiments, the molar ratio of silicon to aluminum in the zeolite composite catalyst is from 6:1 to 28:1 or from 8:1 to 25:1. It will be appreciated that the molar ratio of silicon to aluminum varies depending on the ratio of Mordenite and ZSM-5 in the composite zeolite catalyst. It is noted, the final Si/Al molar ratio in the zeolite composite catalyst depends on the degree of incorporation of the silicon and aluminum species into the final crystalline zeolite. Due to the basicity of the synthesis media, a small fraction of the starting silicon may remain in solution and may not be incorporated in the zeolitic framework thereby decreasing the final Si/Al ratio of the zeolite composite catalyst as compared to the starting Si/Al ratio in the catalyst gel.

From a property standpoint, in one or more embodiments, the composite zeolite catalyst may have a micropore volume ($V_{micro}$) of at least 0.10 cubic centimeters per gram (cm$^3$/g), or a micropore volume of at least 0.12 cm$^3$/g, a micropore volume of 0.10 to 0.25 cm$^3$/g, or a micropore volume of 0.15 to 0.20 cm$^3$/g. The micropore volume may be calculated by the t-plot method of determining micropore volume known to one having skill in the art. Similarly, in one or more embodiments, the composite zeolite catalyst may have a mesopore volume ($V_{meso}$) of at least 0.10 cubic centimeters per gram (cm$^3$/g), or a mesopore volume of at least 0.15 cm$^3$/g, or a mesopore volume of 0.1 to 0.25 cm$^3$/g. The mesopore volume may be calculated according to the Barrett-Joiner-Halenda (BJH) method of determining mesopore volume known to one having skill in the art. Details regarding the t-plot method and the BJH method of calculating micropore volume and mesopore volume respectively are provided in Galarneau et al., "Validity of the t-plot Method to Assess Microporosity in Hierarchical Micro/Mesoporous Materials", Langmuir 2014, 30, 13266-13274, for example.

The micropore volume and the mesopore volume represent the specific volumes corresponding to the microporous structure and to the mesoporous structure, respectively. The mesopores are mainly due to intercrystalline voids formed because of the very small size of the zeolite crystals. The pore size ranges for mesopores and micropores are in conformity with conventionally understood size ranges for such pore classifications with micropores representing pores under 2 nanometers (nm) in diameter and mesopores representing pores of 2 to 50 nm in diameter. A total pore volume would additionally include any macropores if present.

In one or more embodiments, the composite zeolite catalyst may have a surface area defined by a Brunauer-Emmett-Teller (BET) analysis ($S_{BET}$) of at least 350 square meters per gram (m$^2$/g), a $S_{BET}$ surface area of at least 400 m$^2$/g, or a $S_{BET}$ surface area of at least 430 m$^2$/g. Further, the composite zeolite catalyst may have a micropore surface area ($S_{micro}$) of 280 m$^2$/g to 370 m$^2$/g. The micropore surface area may be calculated directly from the micropore volume. Additionally, the zeolite composite catalyst may have an external surface area ($S_{Ext}$) of at least 70 m$^2$/g, and preferentially, it may have an external surface area of 85 m$^2$/g to 170 m$^2$/g. It is noted that the external surface area is obtained as the difference between the BET surface area and the micropore surface area.

The composite zeolite catalyst allows conversion of heavy reformate, or other aromatic reactant streams, in a single reactor. Specifically, the dealkylation of MEB and the transalkylation of the produced toluene with TMB may be performed in a single reactor because of the contact between the crystals of Mordenite and ZSM-5 at the nanometer scale. The MEB dealkylation reaction is necessary in order to obtain the toluene that has to react with the TMB in the feed for producing the desired xylenes. Thus, the contact between the crystals of Mordenite and ZSM-5 at the nanometer scale obtained by the synthesis in a single vessel with simultaneous ZSM-5 and Mordenite formation (one pot synthesis) of the composite zeolite catalyst particles enables an improved and faster coupling of both consecutive reactions as compared with conventional multizeolite catalysts.

Alkylaromatics, such as those present in a heavy reformate (MEB, TMB), in the presence of an acid catalyst, may undergo undesired reactions which lead to formation of aromatics with more than 10 carbon atoms ($A_{10+}$). If these $A_{10+}$ compounds cannot diffuse out of the zeolite crystals through the pores of the crystalline structure because of steric limitations, they may block part of the channel systems or lead to bulkier coke precursors. The improved conversion efficiency of the composite zeolite catalysts alleviates the formation of heavy alkylaromatics. Specifically, the proximity of the ZSM-5 and Mordenite allows the TMB of the feed to react preferentially with the toluene formed by dealkylation of MEB on the ZSM-5 crystals, instead of reacting with other TMB by transalkylation to form tetramethylbenzene or heavier compounds. Additionally, the small crystal size of ZSM-5 and Mordenite, and therefore short diffusion pathways, allow any undesirable products to diffuse out of the zeolite crystals before being able to react and form heavier aromatics, coke precursors, or both. The specific properties of the composite zeolite catalyst, including small crystal size and intimate proximity of the ZSM-5 and Mordenite at the nanometer scale, results in higher selectivity to xylenes and reduced formation of $A_{10+}$ and coke precursors, leading therefore to improved catalyst life.

EXAMPLES

The described embodiments will be further clarified by the following examples and comparative examples.

For demonstration purposes, composite zeolite catalysts were prepared in accordance with one or more embodiments of this disclosure. The composite zeolite catalysts were formed with varying ratios of Mordenite and ZSM-5. Composite zeolite catalyst particles were synthesized with a weight ratio of 40% Mordenite and 60% ZSM-5 and designated MOR<ZSM-5 (Example 1) by using the gel molar composition provided in Table 1 (0.30 Na$_2$O:1 SiO$_2$: 0.025 Al$_2$O$_3$:0.075 C$_{22\text{-}6\text{-}6}$Br$_2$: 40 H$_2$O) and following the same procedure described for Example 2. Composite zeolite catalyst particles were also synthesized with a weight ratio of 75% Mordenite and 25% ZSM-5 and designated MOR>ZSM-5 (Example 2). To synthesize the composite zeolite catalyst particles for Example 2, 0.434 grams (g) of NaAlO$_2$ (Al$_2$O$_3$ 47 wt. %, Na$_2$O 34.4 wt. % and H$_2$O 18.6 wt. %) were added to 4.474 g of a solution of NaOH (10 wt. %) followed by 22.189 g of water. Additionally C$_{22\text{-}6\text{-}6}$Br$_2$ (2.173 g. molar weight=724.48 g/mol) was added as an organic structure-directing agent. Finally 6.009 g of the silicon source (Ludox AS-40, Sigma-Aldrich) was added to the catalyst precursor gel while stirring constantly in order to obtain the desired gel molar composition provided in Table 1 (0.20 Na$_2$O:1 SiO$_2$:0.05 Al$_2$O$_3$: 0.075 C$_{22\text{-}6\text{-}6}$Br$_2$: 40 H$_2$O). The gel with the desired composition was introduced into a Teflon-lined autoclave at 150° C. under stirring at 60 rpm and autogenous pressure for 14 days. In a final step, the resultant powder from the Teflon-lined autoclave was filtered and washed with hot water (50° C.), and dried in an oven at 100° C. overnight. The solid obtained was calcined at 500° C. for 12 hours under air flow. The acid zeolite was obtained by ion exchange with NH$_4$Cl (2.5M solution at 80° C. for 2 hours) and calcinated with air flow at 500° C. for 8 hours. The synthesis gels for the rest of the composite zeolite catalyst particles were prepared in a similar way with the ratio of components adjusted to match the molar ratios provided in Table 1.

TABLE 1

Gel Compositions

| Sample | Composition |
|---|---|
| Example 1 (Si/Al = 12.9) 40 wt. % MOR 60 wt % ZSM-5 | 0.30 $Na_2O$:1 $SiO_2$:0.025 $Al_2O_3$:0.075 $C_{22-6-6}Br_2$:40 $H_2O$ |
| Example 2 (Si/Al = 8.1) 75 wt. % MOR 25 wt. % ZSM-5 | 0.20 $Na_2O$:1 $SiO_2$:0.05 $Al_2O_3$:0.075 $C_{22-6-6}Br_2$:40 $H_2O$ |

Composite zeolite catalyst particles were also synthesized with rhenium incorporated into the catalyst particles. Rhenium was incorporated into Example 1 and Example 2 to generate samples designated as Re/MOR<ZSM-5 (Example 3) and Re/MOR>ZSM-5 (Example 4) respectively. Rhenium was incorporated into all of the samples at 0.3 wt. % by means of the incipient wetness procedure using ammonium perrhenate ($NH_4ReO_4$) as a metal precursor.

Comparative zeolite catalyst samples were also prepared for comparison with the composite zeolite catalyst particles. ATA-21 (Comparative Example 5) represents a physical mixture of Mordenite and ZSM-5, CBV21A (Zeolyst Int.) represents commercially available Mordenite (Comparative Example 6), and CBV3024E (Zeolyst Int.) represents commercially available ZSM-5 (Comparative Example 7). Samples of the commercially available pure Mordenite and ZSM-5 were also prepared with rhenium incorporated into each catalyst. As with the composite zeolite catalyst particles, rhenium was incorporated into each sample to generate samples designated as Re/CBV21A (Comparative Example 8) and Re/CBV3024E (Comparative Example 9). Rhenium was incorporated into all of the samples at 0.3 wt. % by means of the incipient wetness procedure using ammonium perrhenate ($NH_4ReO_4$) as a metal precursor. An additional comparative zeolite catalyst was Re/CBV21A+ Re/CBV3024E (60 wt. % commercially available Mordenite with 0.3 wt. % rhenium and 40 wt. % commercially available ZSM-5 with 0.3 wt. % rhenium physically mixed) (Comparative Example 10).

A listing of the composition of each Example is provided in Table 2.

TABLE 2

Composition of each Example

| EXAMPLE | COMPOSITION |
|---|---|
| Example 1 | MOR < ZSM-5 (40 wt. % Mordenite and 60 wt. % ZSM-5 composite) |
| Example 2 | MOR > ZSM-5 (75 wt % Mordenite and 25 wt. % ZSM-5 composite) |
| Example 3 | Re/MOR < ZSM-5 (40 wt. % Mordenite and 60 wt % ZSM-5 composite with 0.3 wt % rhenium) |
| Example 4 | Re/MOR > ZSM-5 (75 wt. % Mordenite and 25 wt. % ZSM-5 composite with 0.3 wt % rhenium) |
| Comparative Example 5 | ATA-21 |
| Comparative Example 6 | CBV21A (Commercial Mordenite) |
| Comparative Example 7 | CBV3024E (Commercial ZSM-5) |
| Comparative Example 8 | CBV21A with 0.3 wt. % rhenium |
| Comparative Example 9 | CBV3024E with 0.3 wt. % rhenium |
| Comparative Example 10 | 60 wt % CBV21A with 0.3 wt. % rhenium and 40 wt. % CBV3024E with 0.3 wt % rhenium physically mixed |

Figure 1:
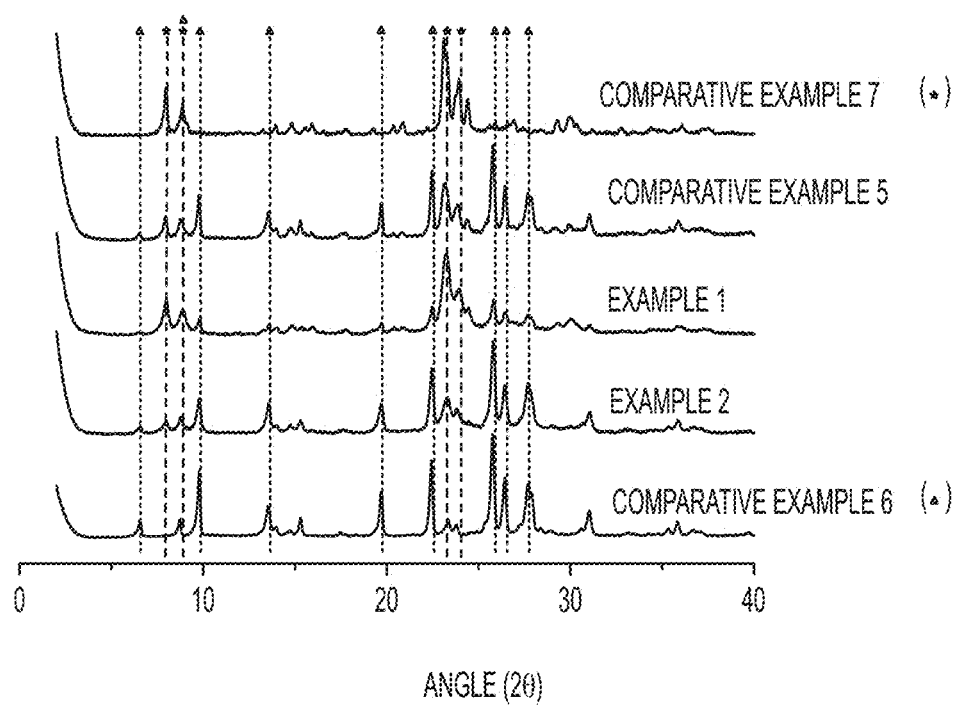
FIG. 1 is an X-Ray Diffraction (XRD) pattern of composite zeolite catalysts synthesized in accordance with one or more embodiments of the present disclosure and comparative commercially available catalysts.

The XRD of Example 1, Example 2, Comparative Example 5, Comparative Example 6, and Comparative Example 7 are provided as FIG. 1 with the distinct peaks for Mordenite and ZSM-5 visible in the composite zeolite catalyst particles (Examples 1 and 2) and the ATA-21 sample (Comparative Examples 5).

The physico-chemical properties of each of the samples were quantified. Specifically, the silicon to aluminum ratio as well as the final wt. % of Re in each sample was determined for each sample type. Additionally, the micropore volume and the mesopore volume were calculated according to the t-plot method and the BJH correlation method respectively. Further, the micropore surface area was calculated from the micropore volume, the total specific surface area was calculated in accordance with the Brunauer-Emmett-Teller (BET) method widely used for evaluating the surface area of porous and finely-divided materials, and the external surface area was calculated based on the difference between the total specific surface area and the micropore surface area. These physio-chemical properties are delineated in Table 3 provide infra.

TABLE 3

Chemical composition and textural properties of samples.

| Sample | Si/Al | Re (wt. %) | $S_{BET}$ ($m^2$/g) | $S_{micro}$ ($m^2$/g) | $S_{Ext}$ ($m^2$/g) | $V_{macro}$ ($cm^3$/g) | $V_{meso}$ ($cm^3$/g) |
|---|---|---|---|---|---|---|---|
| Comp. Example 5 (ATA-21) | 1.9 | — | 362 | 259 | 103 | 0.126 | 0.170 |
| Comp. Example 6 (CBV21A) | 10.1 | — | 451 | 425 | 26 | 0.204 | 0.029 |
| Comp. Example 8 (Re/CBV21A) | 8.9 | 0.3 | 429 | 408 | 21 | 0.200 | 0.027 |
| Example 2 (MOR > ZSM-5) | 8.1 | — | 456 | 371 | 86 | 0.181 | 0.143 |
| Example 4 (Re/MOR > ZSM-5) | 8.0 | 0.3 | 433 | 350 | 83 | 0.170 | 0.144 |
| Example 1 (MOR < ZSM-5) | 12.9 | — | 440 | 316 | 124 | 0.153 | 0.206 |
| Example 3 (Re/MOR < ZSM-5) | 12.3 | 0.3 | 423 | 300 | 122 | 0.143 | 0.277 |
| Comp. Example 7 (CBV3024E) | 13.2 | — | 372 | 332 | 40 | 0.162 | 0.055 |

TABLE 3-continued

Chemical composition and textural properties of samples.

| Sample | Si/Al | Re (wt. %) | $S_{BET}$ (m$^2$/g) | $S_{micro}$ (m$^2$/g) | $S_{Ext}$ (m$^2$/g) | $V_{macro}$ (cm$^3$/g) | $V_{meso}$ (cm$^3$/g) |
|---|---|---|---|---|---|---|---|
| Comp. Example 9 (Re/CBV3024E) | 13.4 | 0.3 | 363 | 325 | 38 | 0.158 | 0.052 |

Table 3 illustrates that the Mordenite and ZSM-5 composite zeolite catalysts have properties which correlate with the proportion of Mordenite and ZSM-5 in the final composite zeolite catalyst. The Si/Al ratio, $S_{BET}$, $S_{micro}$, $S_{ext}$, $V_{micro}$, and $V_{meso}$ each follow a generally increasing or decreasing pattern as the ratio of ZSM-5 increases that matches the difference between pure Mordenite (CBV21A) and pure ZSM-5 (CBV3024E). For example, as the proportion of ZSM-5 increases in the composite zeolite catalyst particle sample, the $S_{BET}$ and the micropore volume ($V_{micro}$) decrease in agreement with the $S_{BET}$ and $V_{micro}$ for pure ZSM-5 being lower than for pure Mordenite.

The acidic properties of each of the samples were also quantified. Acidity measurements were carried out by adsorption/desorption of pyridine followed by IR spectroscopy. Self-supported wafers (10 milligrams per square centime (mg/cm$^2$)) of calcined samples, previously activated at 400° C. and 10$^{-2}$ Pascal (Pa) overnight in a Pyrex vacuum cell, were allowed to come in contact with 6.5×10$^2$ Pa of pyridine vapor at room temperature and desorbed in vacuum at increasing temperatures (150° C., 250° C., and 350° C.). The spectra were recorded at room temperature. All the spectra were scaled according to the sample weight. Brønsted and Lewis acidity of the samples compared are given in arbitrary units, according to the intensity of the bands assigned to the pyridine interacting with the Brønsted and Lewis acid sites of the zeolites (1550 and 1450 cm$^{-1}$, respectively). These acidic properties are listed in Table 4 provide infra.

may be compared. The spectra for both before pyridine adsorption (represented as a solid line) and after pyridine adsorption at 150 C (represented as a dotted line) are presented. Comparing the band at 3600 cm-1, which corresponds to the acid hydroxyls, it may be concluded that most of the acid sites of Examples 1 (MOR<ZSM-5) and 2 (MOR>ZSM-5) sample are able to interact with the basic probe molecule, while conversely 40% of the acid sites for Comparative Example 6 (CBV21A) are not accessible to pyridine. Comparing the band at 3745 cm$^{-1}$, which corresponds to external Si—OH, it may be concluded that this band in the spectra of Example 1 (MOR<ZSM-5) and Example 2 (MOR>ZSM-5) is more intense than the commercially available Mordenite sample which is in agreement with the demonstrated higher external surface area.

Figure 5:
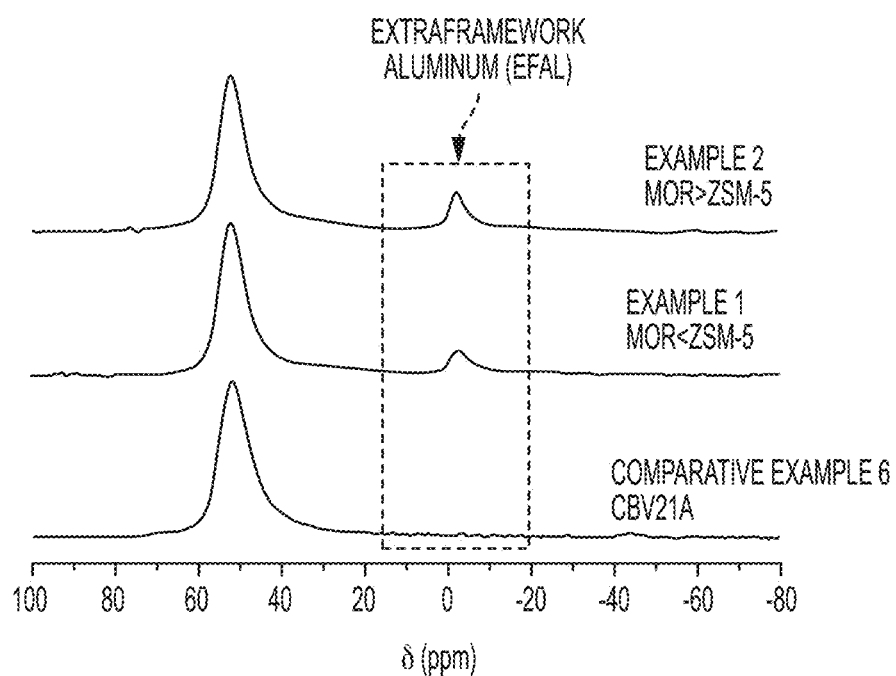
FIG. 5 is a $^{27}$Al-NMR spectra for a commercially available Mordenite, a composite zeolite catalyst with a Mordenite to ZSM-5 ratio of 75:25, and a composite zeolite catalyst with a Mordenite to ZSM-5 ratio of 40:60 synthesized in accordance with one or more embodiments of the present disclosure.

Although pyridine is able to interact with all the acid sites of Examples 1 (MOR<ZSM-5) and 2 (MOR>ZSM-5), it presents a lower Brønsted acid density and higher number of Lewis acid sites in comparison with Comparative Example 6 (CBV21A), although they both present similar Si/Al molar ratio. The difference in Brønsted acid site density and number of Lewis acid sites may be attributed to the presence of extraframework Aluminum (EFAL) with part of the EFAL generating more Lewis acid sites while neutralizing bridging hydroxyl groups, thereby decreasing the Brønsted acid density. With reference to FIG. 5, a $^{27}$Al-NMR spectra, the EFAL in Example 2 (MOR>ZSM-5) is indicated by the band in the dashed box. A smaller band is indicated from Example 1 (MOR<ZSM-5) and no band is indicated for Comparative Example 6 (CBV21A).

TABLE 4

Acidic properties of samples

| Sample | Brønsted Acidity (u.a.) | | | | Lewis Acidity (u.a.) | | |
|---|---|---|---|---|---|---|---|
| | B150 | B250 | B350 | B350/B150 | L150 | L250 | L350 |
| Comp. Example 5 (ATA-21) * | 375 | 296 | 156 | 0.42 | 186 | 169 | 118 |
| Comp. Example 6 (CBV21A) | 618 | 487 | 373 | 0.48 | 51 | — | — |
| Comp. Example 8 (Re/CBV21A) | 400 | 363 | 299 | 0.75 | 65 | — | — |
| Example 2 (MOR > ZSM-5) | 356 | 275 | 184 | 0.52 | 78 | 76 | 76 |
| Example 4 (Re/MOR > ZSM-5) | 292 | 154 | 166 | 0.57 | 49 | — | — |
| Example 1 (MOR < ZSM-5) | 194 | 149 | 112 | 0.58 | 149 | 126 | 126 |
| Example 3 (Re/MOR < ZSM-5) | 238 | 232 | 184 | 0.77 | 220 | 150 | 124 |
| Comp. Example 7 (CBV3024E) | 439 | 395 | 337 | 0.77 | 51 | 36 | 32 |
| Comp. Example 9 (Re/CBV3024E) | 411 | 336 | 293 | 0.71 | 94 | 68 | 61 |

* Normalized to zeolite content as ATA-21 comprises 20 wt. % of non-zeolite matrix.

Figure 4:
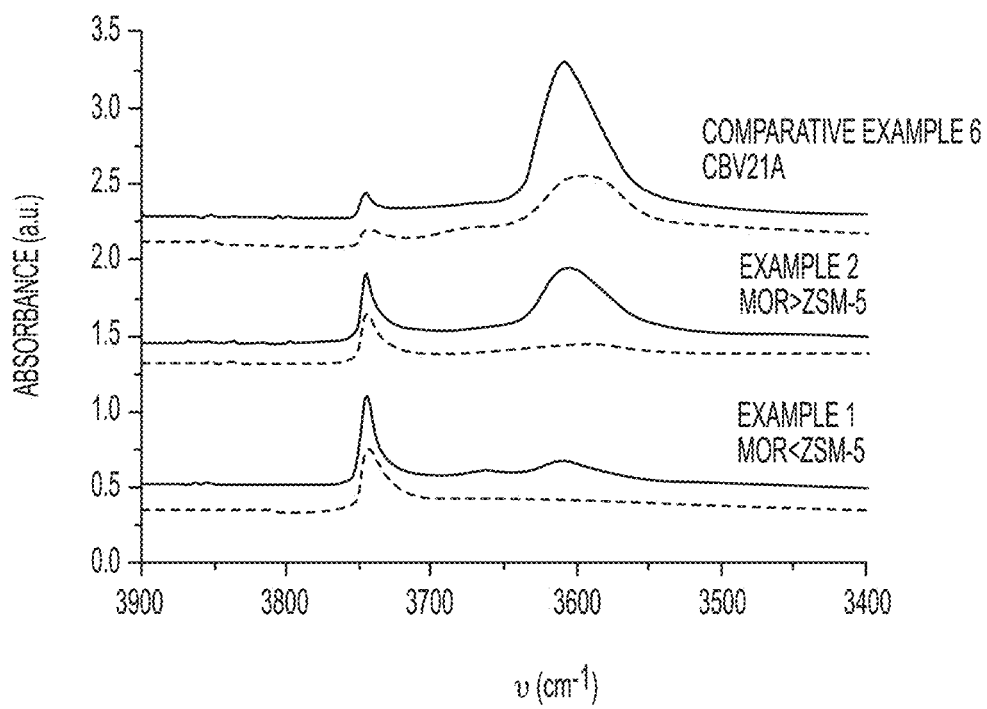
FIG. 4 is a Fourier transform infrared (FT-IR) spectra of commercially available Mordenite, a composite zeolite catalyst with a Mordenite to ZSM-5 ratio of 75:25, and a composite zeolite catalyst with a Mordenite to ZSM-5 ratio of 40:60 synthesized in accordance with one or more embodiments of the present disclosure.

With reference to FIG. 4, a Fourier transformed infrared spectra, the bands from Comparative Example 6 (CBV21A), Example 1 (MOR<ZSM-5) and Example 2 (MOR>ZSM-5)

As stated previously, the present composite zeolite catalyst particles represent a dealkylation and transalkylation catalyst suitable for converting $C_{9+}$ alkyl aromatic hydrocarbons to a product stream comprising benzene, toluene, and xylenes, particularly to commercially valuable xylenes. The feed stream to the conversion process generally comprises alkylaromatic hydrocarbons in the carbon number range $C_9$ to $C_{11+}$ that may include, for example, such hydrocarbons as propylbenzenes, methylethylbenzenes, tetramethylbenzenes, ethyldimethylbenzenes, diethylbenzenes, methylpropylbenzenes, and mixtures thereof. For purposes of testing and quantifying the examples and comparative examples a simulated heavy reformate feed was generated. The simulated heavy reformate feed comprised 30 wt. % para-methylethylbenzene (p-MEB) and 70 wt. % 1,2,4-trimethylbenzene (1,2,4-TMB).

Catalytic test for conversion of the simulated heavy reformate feed were performed in a reaction system comprising sixteen (16) continuous fixed-bed parallel microreactors. Each reactor was capable of being fed independently with the desired flow of the simulated reformate feed and $H_2$ making it possible to operate in a wide range of contact times and hydrogen/hydrocarbon molar ratios. The simultaneous catalytic experiments were carried out under the following conditions: 20 bar total pressure, a hydrogen/hydrocarbon molar ratio of 8.5, a reaction time of 16 hours per temperature, and a weight hourly space velocity (WHSV) of 10 inverse hours ($h^{-1}$). After the testing at each temperature the zeolitic catalysts were kept at that temperature and under $H_2$ atmosphere for an additional 10 hours. Each zeolitic catalyst sample was prepared to a particle size of 0.2 to 0.4 millimeters (mm). The tested zeolitic samples included Example 4 (Re/MOR>ZSM-5) (75:25 molar ratio Mordenite:ZSM-5 with 0.3 wt. % rhenium), synthesized in accordance with the present disclosure, Comparative Example 5 (ATA-21), Comparative Example 8 (Re/CBV21A) and Comparative Example 10 (60 wt % Re/CBV21A+40 wt % Re/CBV3024E). Comparative Example 5 (ATA-21) is a commercially available heavy reformate conversion catalyst based on a physical mixture of Mordenite and ZSM-5 zeolites and serves as a comparative example for the composite zeolite catalysts synthesized in accordance with the present disclosure. Similarly, Comparative Example 8 (Re/CBV21A) is a commercially available Mordenite zeolite and serves as a comparative example for the composite zeolite catalysts synthesized in accordance with the present disclosure. Similarly, Comparative Example 10 (60 wt % Re/CBV21A+40 wt % Re/CBV3024E) is a physical mixture of commercially available Mordenite and ZSM-5 zeolites and serves as a comparative example for the composite zeolite catalysts synthesized in accordance with the present disclosure.

Each fixed-bed microreactor reactor was prepared with 125 mg of the zeolitic catalyst sample and diluted with silicon carbide (SiC) to a total bed volume of 2.0 milliliter (ml) for testing. The experiments were performed on the same zeolite weight basis so the matrix in Comparative Example 5 (ATA-21) was excluded from calculation of the 125 mg by accounting for the 20 wt. % of non-zeolite matrix. Four consecutive reactions phases were completed at temperatures of 350° C., 375° C., 400° C., and a return to 350° C.

The reaction products from each of the fixed-bed microreactors were analyzed by on-line gas chromatography using two independent channels (Bruker 450 Gas Chromatograph). Argon (Ar) as an internal standard, $H_2$, methane, and ethane were analyzed in a first channel equipped with a thermal conductivity detector (TCD) and three columns. The three columns were a Hayesep N pre-column (0.5 meter (m) length) (Hayes Separations, Inc.), a Hayesep Q (1.5 m length) (Hayes Separations. Inc.), and a 13× molecular sieve (1.2 m length). In a second channel the $C_1$-$C_4$ hydrocarbons were first separated from the aromatics in a CP-Wax capillary column (5.0 m length and 0.32 mm inner diameter) (Cole-Parmer). Subsequently, the $C_1$-$C_4$ gases were separated in a column with CP-PoraBOND Q (25 m length and 0.32 mm inner diameter) (Cole-Parmer) and detected in a flame ionization detector (FID). Separation of the aromatics was completed in a second CP-Wax (1.0 m length and 0.32 mm inner diameter) connected to a second FID.

Figure 6:
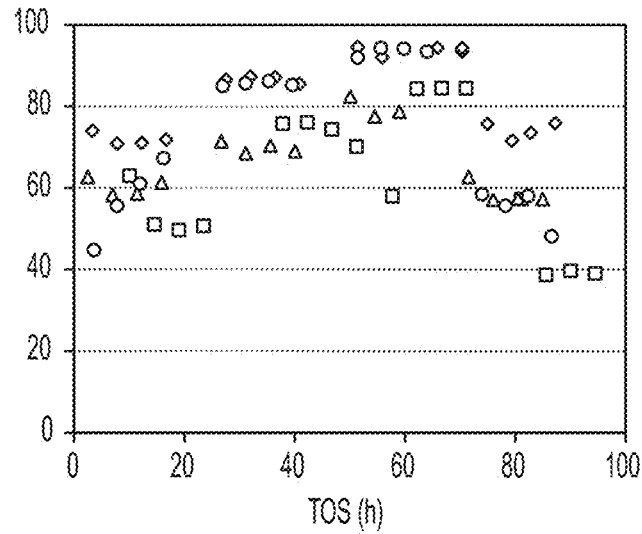
FIG. 6 is a graph of Methylethylbenzene (MEB) conversion of a simulated heavy reformate stream obtained with commercially available zeolite catalysts and composite zeolite catalyst particles synthesized in accordance with one or more embodiments of the present disclosure.
Figure 7:
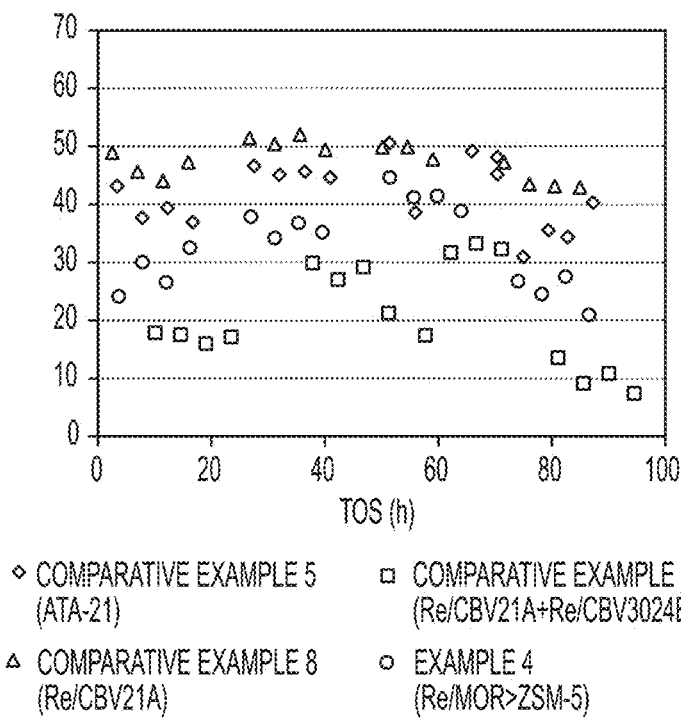
FIG. 7 is a graph of Trimethylbenzene (TMB) conversion of a simulated heavy reformate stream obtained with commercially available zeolite catalysts and composite zeolite catalyst particles synthesized in accordance with one or more embodiments of the present disclosure.
Figure 8:
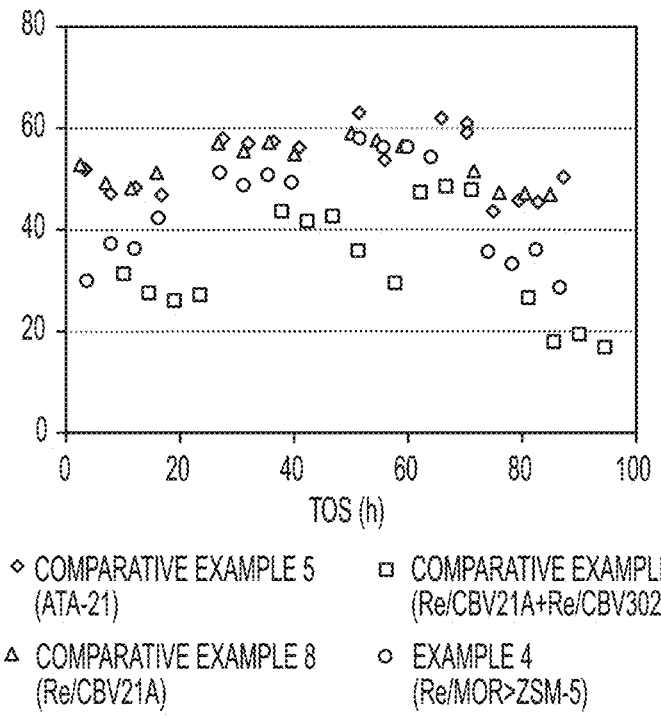
FIG. 8 is a graph of overall conversion (MEB+TMB) of a simulated heavy reformate stream obtained with commercially available zeolite catalysts and composite zeolite catalyst particles synthesized in accordance with one or more embodiments of the present disclosure.
Figure 9:
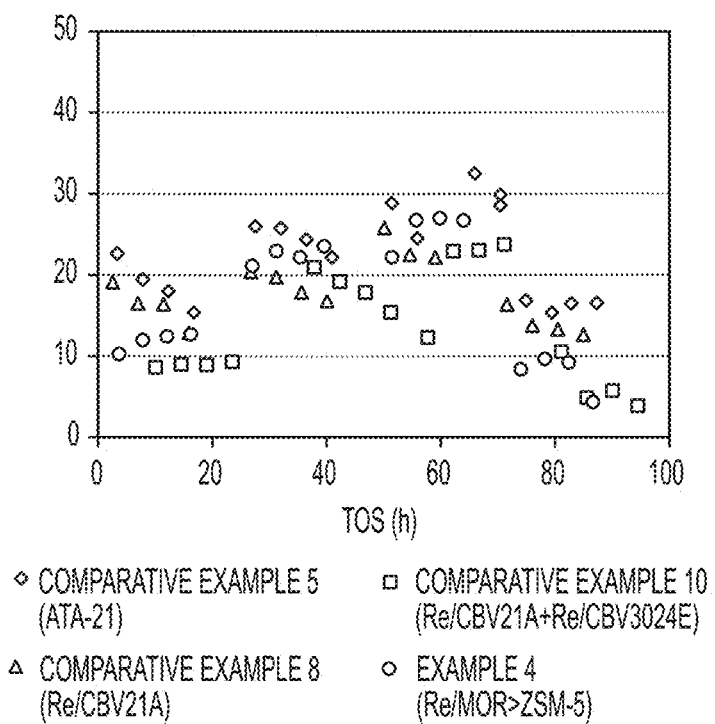
FIG. 9 is a graph of xylenes yield from a simulated heavy reformate stream obtained with commercially available zeolite catalysts and composite zeolite catalyst particles synthesized in accordance with one or more embodiments of the present disclosure.
Figure 10:
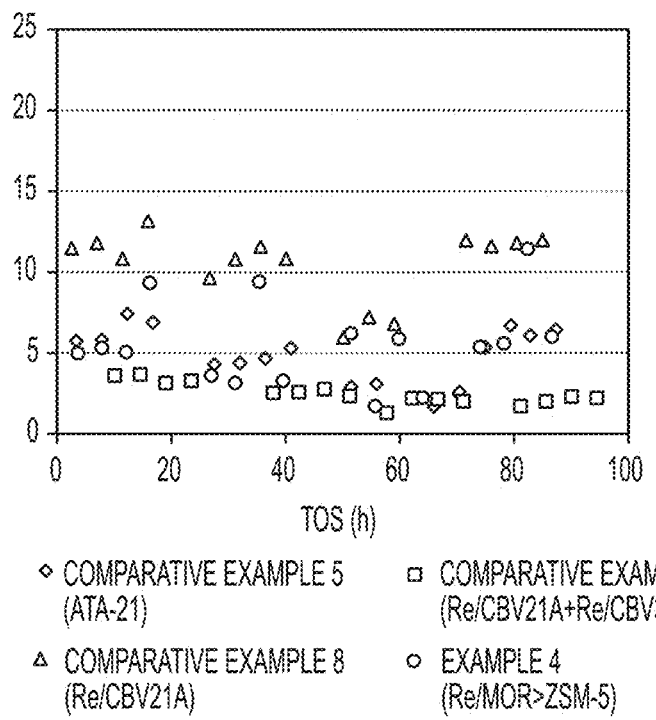
FIG. 10 is a graph of $A_{10}$ yield (yield of aromatics with 10 carbons) from a simulated heavy reformate stream obtained with commercially available zeolite catalysts and composite zeolite catalyst particles synthesized in accordance with one or more embodiments of the present disclosure.

With reference to FIGS. 6, 7 and 8, the MEB conversion (dealkylation). TMB conversion (transalkylation), and overall conversion (MEB+TMB) are illustrated for each of Example 4, Comparative Example 5, Comparative Example 10, and Comparative Example 8 versus time on stream (TOS). It is noted that Example 4 did not exhibit deactivation during the testing procedure. This phenomenon is indicated by the conversion percentage for the initial 350° C. stage at the beginning of each test and the final 350° C. stage at the conclusion of each test being similar.

The lack of deactivation observed for the composite zeolite catalyst is believed to be due to their higher catalytic efficiency, which reduces the formation of heavy alkylaromatics. The proximity of the two zeolite phases, ZSM-5 and Mordenite, allows the TMB present in the feed to preferentially react on the Mordenite crystals with the toluene previously formed by dealkylation of MEB on the ZSM-5 crystals. When the ZSM-5 and Mordenite zeolite crystals are not so intimately mixed as in the physically mixed catalyst, TMB may react with other TMB by transalkylation to tetramethylbenzene or heavier compounds. Additionally, the small crystal size of ZSM-5 and Mordenite creates short diffusion pathways which allow the products to diffuse out of the zeolite crystals before undergoing reactions into heavier aromatics, coke precursors, or both. This reduced formation of $A_{10+}$ and coke precursors leads to improved catalyst life.

Figure 11:
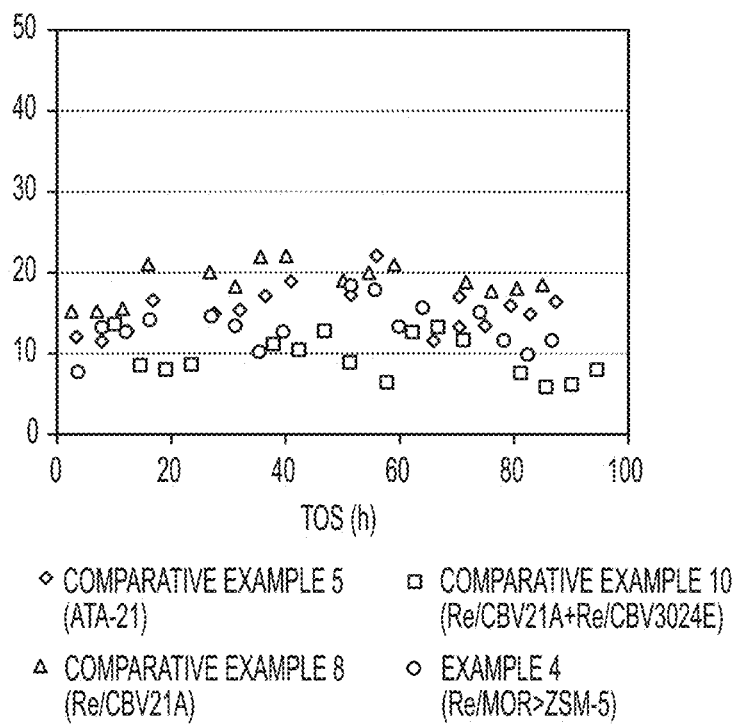
FIG. 11 is a graph of $A_{10+}$ yield (yield of aromatics with more than 10 carbons) from a simulated heavy reformate stream obtained with commercially available zeolite catalysts and composite zeolite catalyst particles synthesized in accordance with one or more embodiments of the present disclosure.
Figure 12:
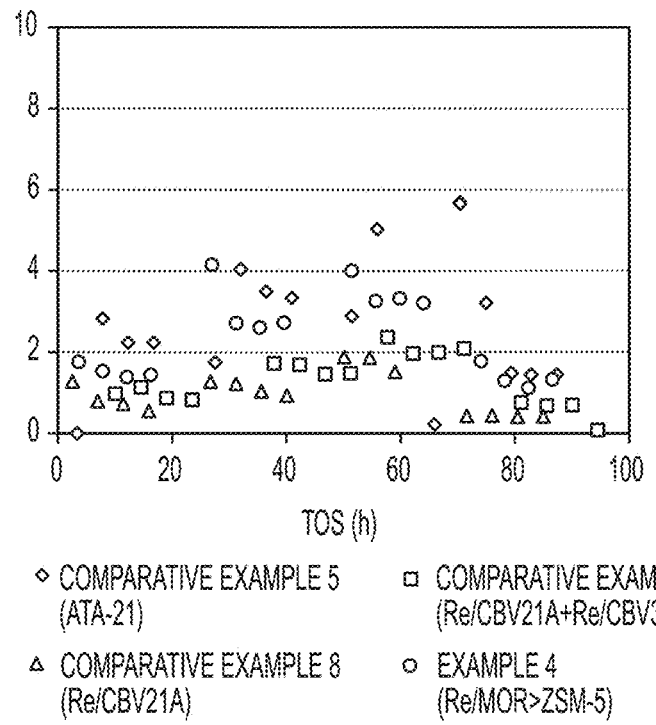
FIG. 12 is a graph of light hydrocarbon yield from a simulated heavy reformate stream obtained with commercially available zeolite catalysts and composite zeolite catalyst particles synthesized in accordance with one or more embodiments of the present disclosure.
Figure 13:
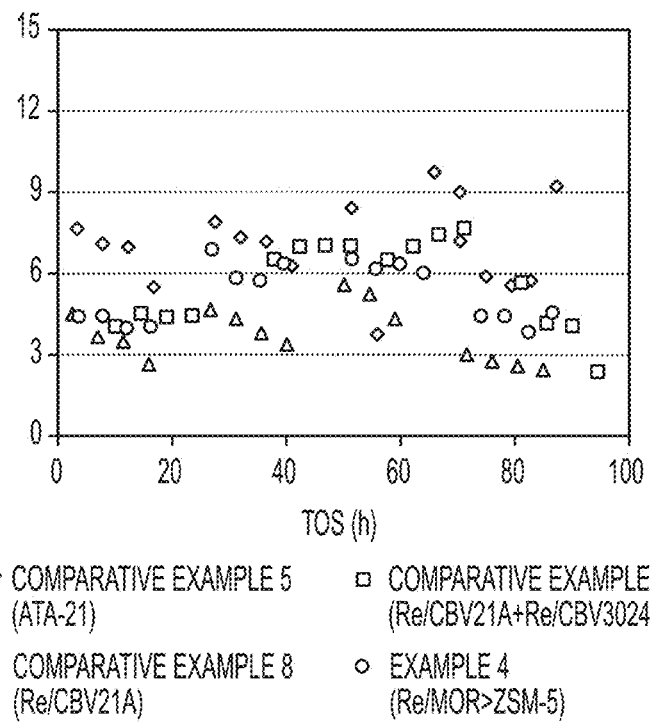
FIG. 13 is a graph of toluene yield from of a simulated heavy reformate stream obtained with commercially available zeolite catalysts and composite zeolite catalyst particles synthesized in accordance with one or more embodiments of the present disclosure.
Figure 14:
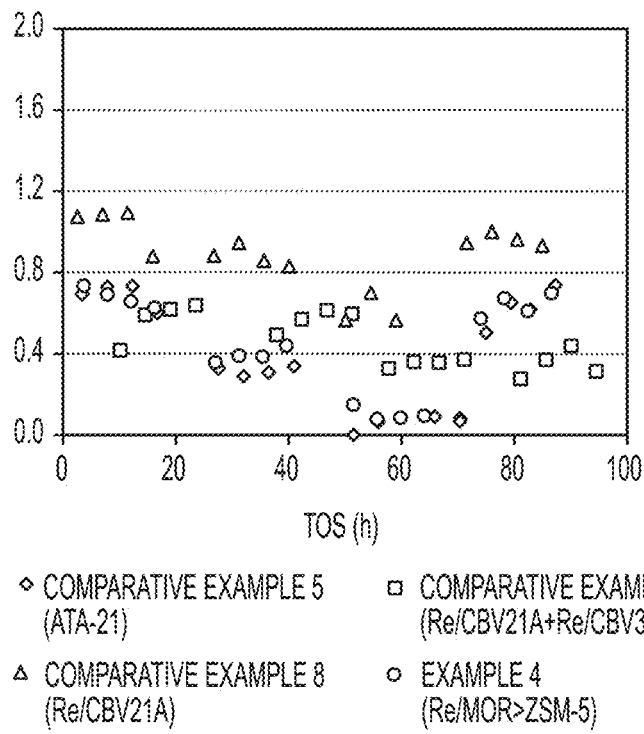
FIG. 14 is a graph of ethylbenzene yield from a simulated heavy reformate stream obtained with commercially available zeolite catalysts and composite zeolite catalyst particles synthesized in accordance with one or more embodiments of the present disclosure.
Figure 15:
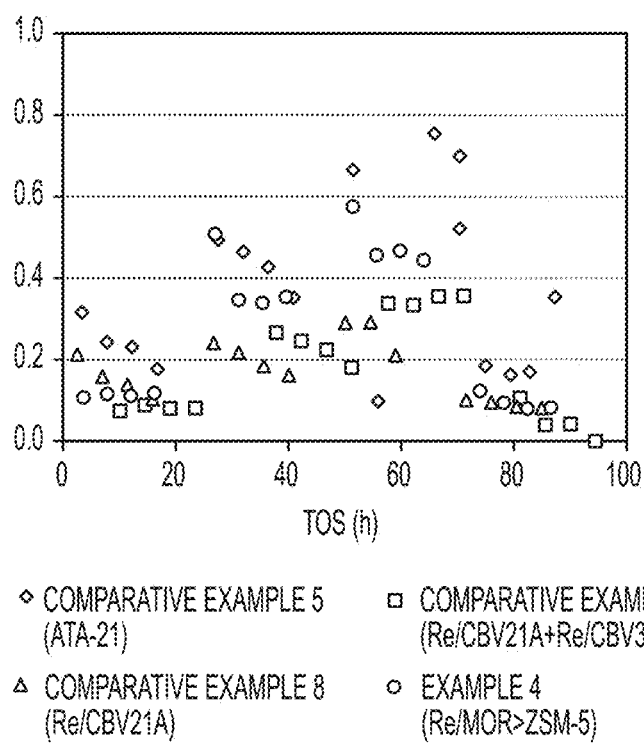
FIG. 15 is a graph of benzene yield from a simulated heavy reformate stream obtained with commercially available zeolite catalysts and composite zeolite catalyst particles synthesized in accordance with one or more embodiments of the present disclosure.

With reference to FIGS. 9, 10, 11, 12, 13, 14 and 15, the xylenes yield, $A_{10}$ yield. $A_{10+}$ yield, light hydrocarbon yield, toluene yield, ethylbenzene yield, and benzene yield are respectively illustrated for each of the 4 sample types versus TOS. It is noted that Example 4 (Re/MOR>ZSM-5) favors the xylenes production as compared to Comparative Example 8 (Re/CBV21A) and has a similar xylenes production as that of Comparative Example 5 (ATA-21). The higher selectivity to xylenes is believed a consequence of the lower production of undesirable $A_{10+}$ aromatics. As indicated in FIG. 11, Example 4 (Re/MOR>ZSM-5) demonstrated the lowest yield of $A_{10+}$ aromatics.

The results generated from testing the samples with the simulated heavy reformate provided information regarding the relative activity of the different catalyst compositions and their stability towards deactivation with an extended TOS. The catalysts were also tested under conditions closer to industrial conditions which would be observed for conversion of heavy reformate to xylenes. To more accurately reflect industrial conditions a supply of actual industrial heavy reformate with known composition was utilized. Table 5 delineates the composition of the industrial heavy reformate used for testing and Table 6 provides the relative ratios of various components.

TABLE 5

Industrial Heavy Reformate Composition

| Component | | |
|---|---|---|
| Hydrocarbon Type | Hydrocarbon Sub-Type | Mass % |
| $A_8$ | Total | 3.94 |
| | Ethylbenzene | 0.03 |
| | p-xylene | 0.15 |
| | m-xylene | 0.38 |
| | o-xylene | 3.38 |
| $A_9$ | Total | 82.75 |
| | Isopropylbenzene Total | 0.43 |
| | n-propylbenzene Total | 2.07 |
| | Methylethylbenzene Total | 19.62 |
| | (MEB)  m- and p-MEB | 15.33 |
| | o-MEB | 4.29 |
| | Trimethylbenzene Total | 60.63 |
| | (TMB)  1,3,5-TMB | 11.69 |
| | 1,2,4-TMB | 40.81 |
| | 1,2,3-TMB | 8.13 |
| $A_{10+}$ | Total | 13.33 |

TABLE 6

Industrial Heavy Reformate Composition Ratio

| | | |
|---|---|---|
| $A_8$ | Ethylbenzene:Total $A_8$ | 0.0076 |
| | p-xylene:Total $A_8$ | 0.038 |
| | m-xylene:Total $A_8$ | 0.096 |
| | o-xylene:Total $A_8$ | 0.858 |
| $A_9$ | Isopropylbenzene:Total $A_9$ | 0.0052 |
| | n-propylbenzene:Total $A_9$ | 0.025 |
| | Total Methylethylbenzene (MEB):Total $A_9$ | 0.237 |
| | m- and p-MEB:Total $A_9$ | 0.185 |
| | o-MEB:Total $A_9$ | 0.052 |
| | m- and p-MEB:Total MEB | 0.781 |
| | o-MEB:Total MEB | 0.219 |
| | Total Trimethylbenzene (TMB):Total $A_9$ | 0.733 |
| | 1,3,5-TMB:Total $A_9$ | 0.141 |
| | 1,2,4-TMB:Total $A_9$ | 0.493 |
| | 1,2,3-TMB:Total $A_9$ | 0.098 |
| | 1,3,5-TMB:Total TMB | 0.193 |
| | 1,2,4-TMB:Total TMB | 0.673 |
| | 1,2,3-TMB:Total TMB | 0.124 |
| | Total $A_9$:Total $A_{10+}$ | 6.21 |

Catalytic test for conversion of the industrial heavy reformate feed were performed in a fixed-bed stainless-steel tubular reactor. The reactor had a 10.5 mm internal diameter and a 20 centimeter (cm) length. The catalytic experiments in the fixed-bed tubular reactor were carried out under the following conditions: 20 bar total pressure, a hydrogen/hydrocarbon molar ratio of 4:1, and a weight hourly space velocity (WHSV) of 10 $h^{-1}$. The reactor was charged with 0.75 grams (g) of catalyst with a particle size of 0.2 to 0.4 mm for each test. The tested zeolitic samples included Example 4, Comparative Example 5. Comparative Example 8, and Comparative Example 10. The catalyst was diluted with SiC to bring the total volume up to a total bed volume of 5.0 ml. For Comparative Example 5 (ATA-21), the amount of catalyst added was adjusted according to their zeolite content in order to have 0.75 g of zeolite (the matrix was excluded). Gaseous compounds ($H_2$, $N_2$) were fed into the system by mass flow meters via a vaporizer. Nitrogen was also fed into the system as an internal reference. The industrial heavy reformate was fed by means of a high performance liquid chromatography (HPLC) pump to the vaporizer. The vaporizer was operated at 300° C. and provided a steady and non-pulsing flow of reactants to the reactor. Prior to commencing the catalytic test, the catalyst was reduced in situ at 450° C. for 1 h under $H_2$ flow (50 ml/min) at atmospheric pressure. For the catalytic testing, four consecutive reactions phases were completed at temperatures of 350° C. (7 h total), 375° C. (5 h total), 400° C. (5 h total), and a return to 350° C. (5 h total).

During reaction, the effluent stream was analyzed on-line at intervals of 32 minutes (min) in a Varian CP3800 equipped with two detection channels. The first channel was equipped with a thermal conductivity detector (TCD), and allowed separation, identification and quantification of permanent gases and light hydrocarbons ($C_1$-$C_5$). The heavier hydrocarbons ($C_{6+}$) were separated in a WAX-type capillary column having a 60 m length and 0.2 mm inner diameter and detected by a flame ionization detector (FID). A Wax capillary column is a capillary column where polyethylene glycols are used as the stationary phase and is specially indicated for separation of aromatic compounds. Nitrogen was employed as an internal reference allowing an accurate quantification of the amount and distribution of reaction products.

Figure 16:
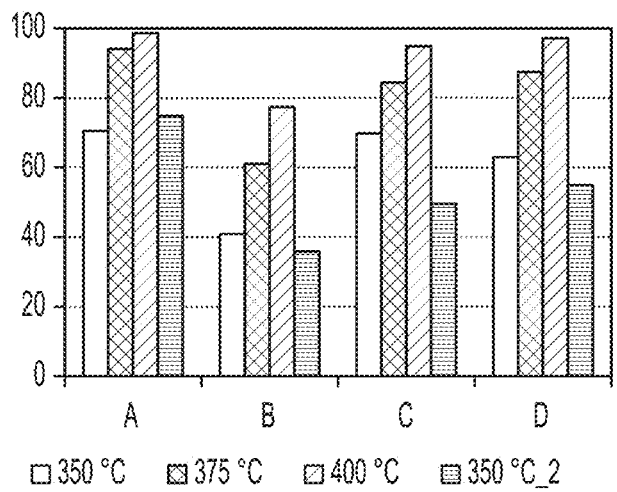
FIG. 16 is a graph of MEB conversion of an industrial heavy reformate stream obtained with commercially available zeolite catalysts and composite zeolite catalyst particles synthesized in accordance with one or more embodiments of the present disclosure.
Figure 17:
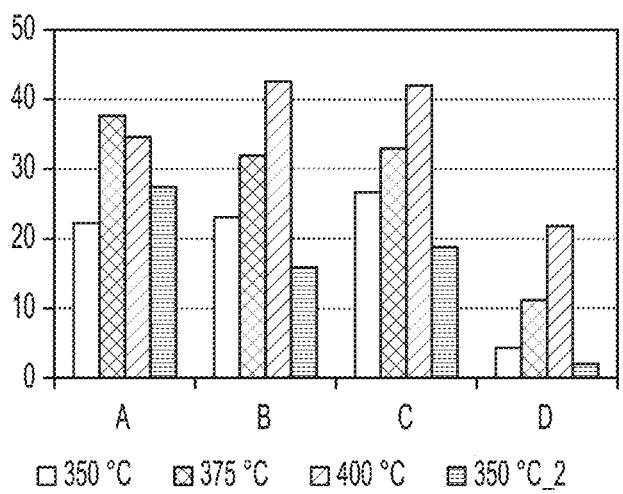
FIG. 17 is a graph of TMB conversion of an industrial heavy reformate stream obtained with commercially available zeolite catalysts and composite zeolite catalyst particles synthesized in accordance with one or more embodiments of the present disclosure.
Figure 18:
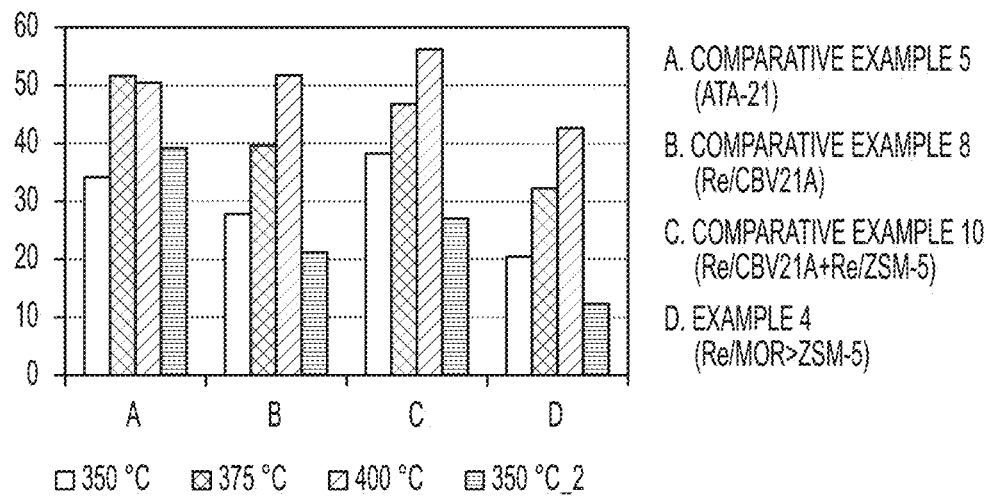
FIG. 18 is a graph of overall conversion of an industrial heavy reformate stream obtained with commercially available zeolite catalysts and composite zeolite catalyst particles synthesized in accordance with one or more embodiments of the present disclosure.
Figure 19:
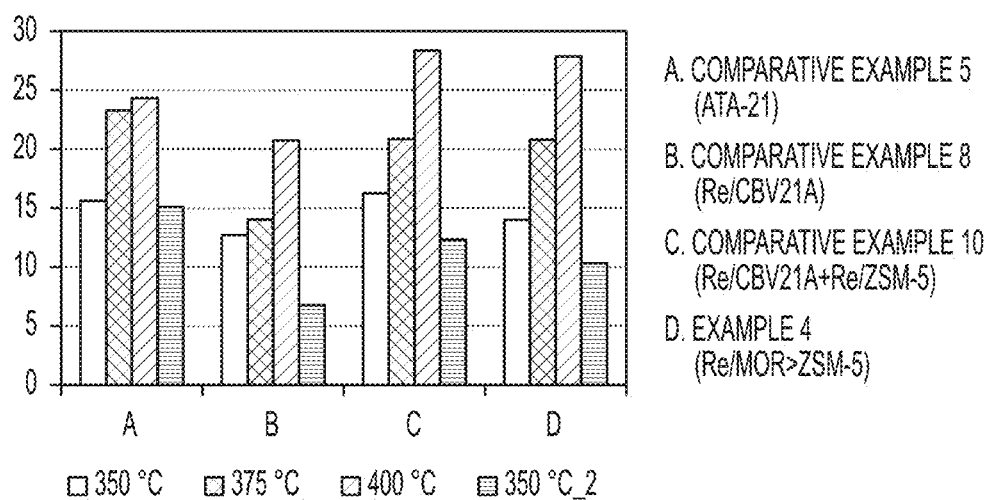
FIG. 19 is a graph of xylenes yield from an industrial heavy reformate stream obtained with commercially available zeolite catalysts and composite zeolite catalyst particles synthesized in accordance with one or more embodiments of the present disclosure.
Figure 20:
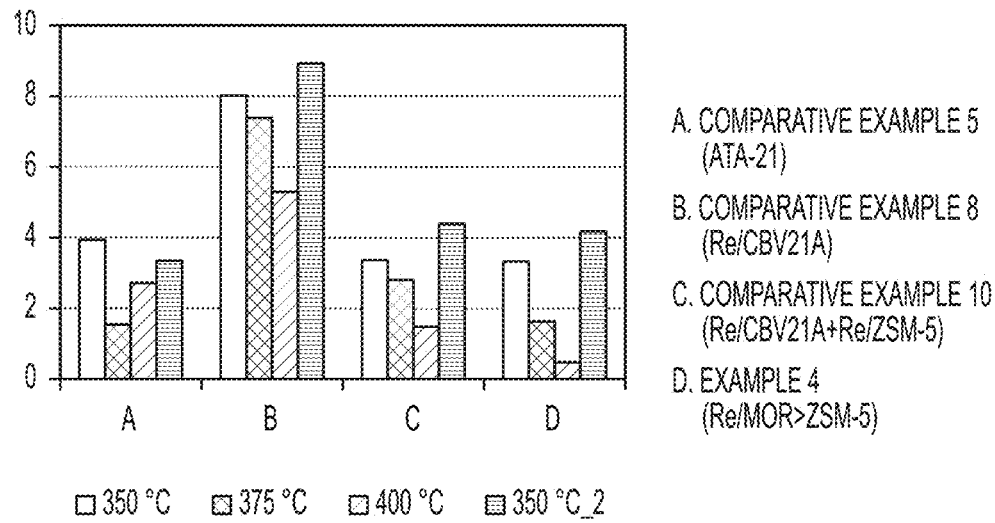
FIG. 20 is a graph of $A_{10}$ yield from an industrial heavy reformate stream obtained with commercially available zeolite catalysts and composite zeolite catalyst particles synthesized in accordance with one or more embodiments of the present disclosure.
Figure 21:
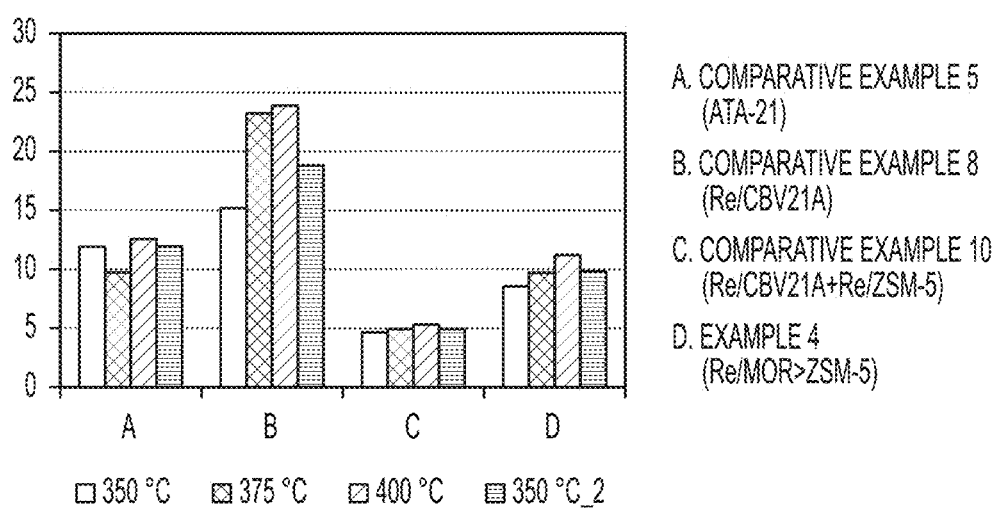
FIG. 21 is a graph of $A_{10+}$ yield from an industrial heavy reformate stream obtained with commercially available zeolite catalysts and composite zeolite catalyst particles synthesized in accordance with one or more embodiments of the present disclosure.
Figure 22:
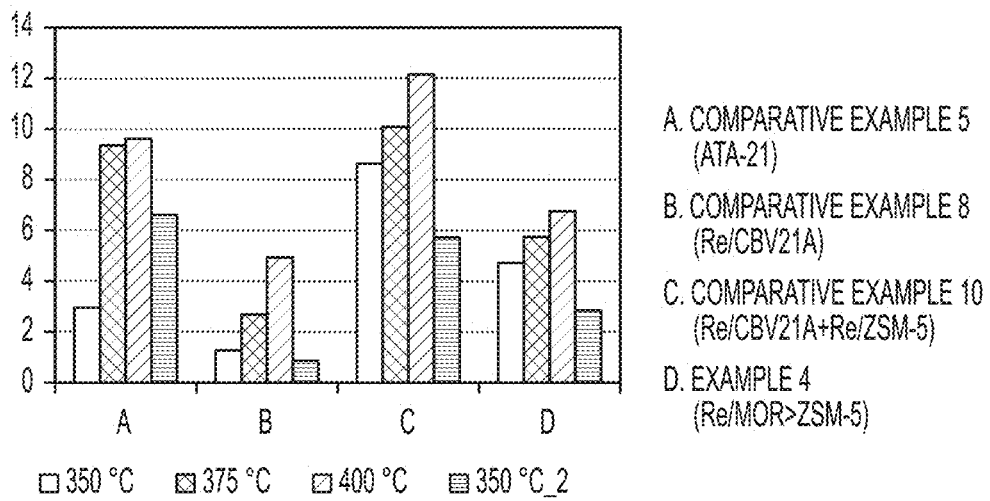
FIG. 22 is a graph of light hydrocarbon yield from an industrial heavy reformate stream obtained with commercially available zeolite catalysts and composite zeolite catalyst particles synthesized in accordance with one or more embodiments of the present disclosure.
Figure 23:
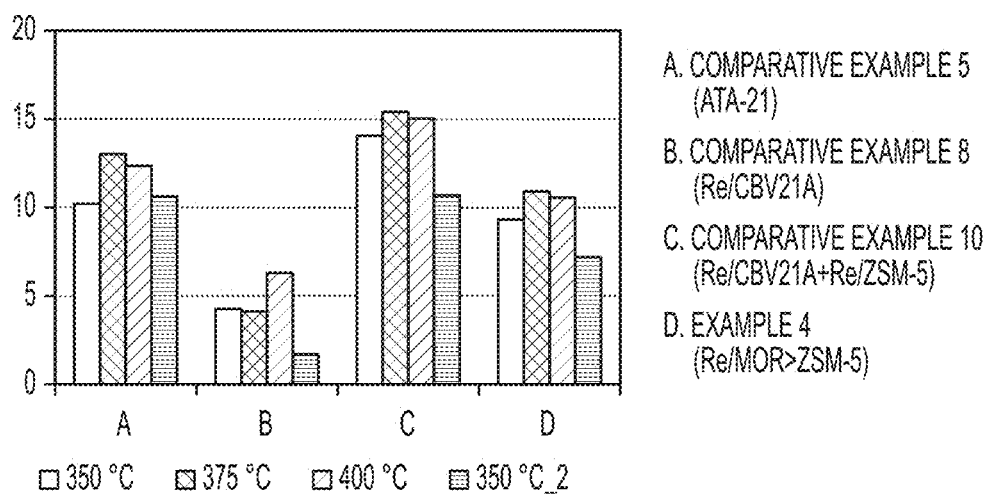
FIG. 23 is a graph of toluene yield from of an industrial heavy reformate stream obtained with commercially available zeolite catalysts and composite zeolite catalyst particles synthesized in accordance with one or more embodiments of the present disclosure.
Figure 24:
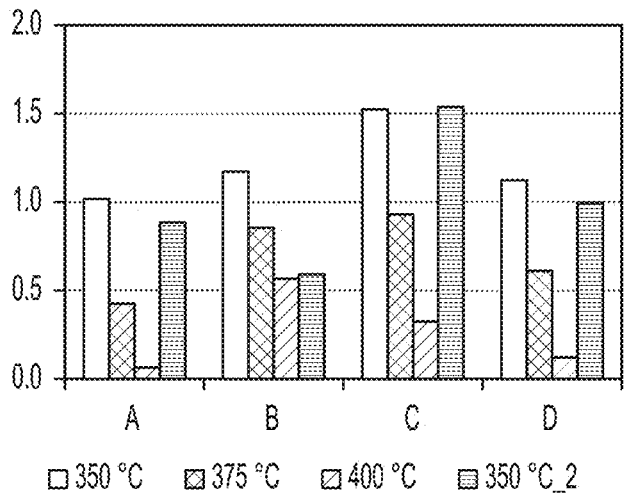
FIG. 24 is a graph of ethylbenzene yield from an industrial heavy reformate stream obtained with commercially available zeolite catalysts and composite zeolite catalyst particles synthesized in accordance with one or more embodiments of the present disclosure.
Figure 25:
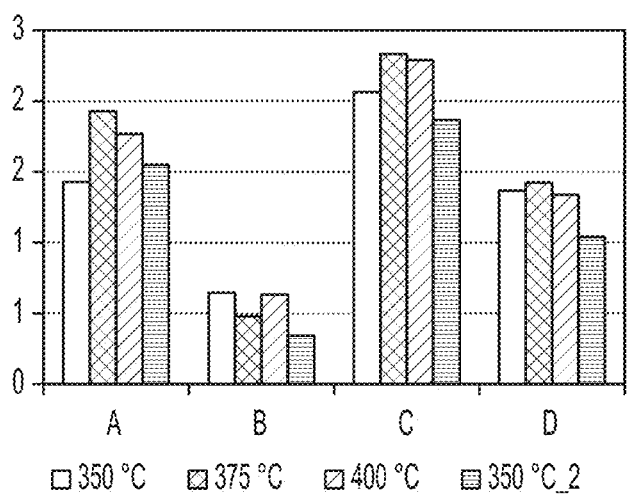
FIG. 25 is a graph of benzene yield from an industrial heavy reformate stream obtained with commercially available zeolite catalysts and composite zeolite catalyst particles synthesized in accordance with one or more embodiments of the present disclosure.
Figure 26:
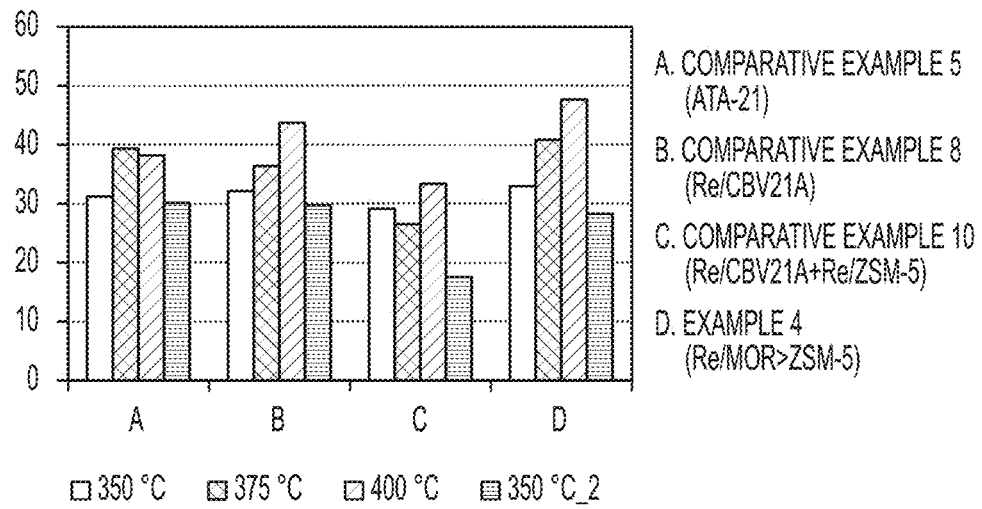
FIG. 26 is a graph of xylenes selectivity from an industrial heavy reformate stream obtained with commercially available zeolite catalysts and composite zeolite catalyst particles synthesized in accordance with one or more embodiments of the present disclosure.
Figure 27:
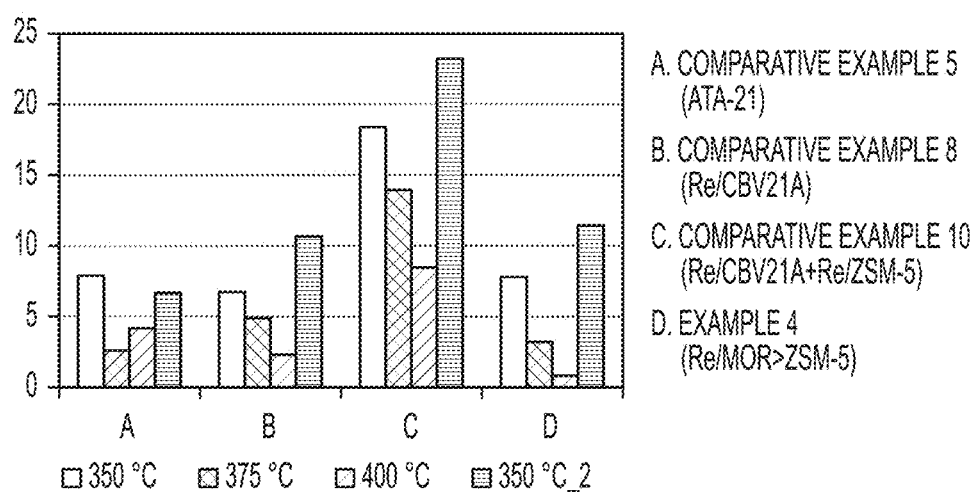
FIG. 27 is a graph of $A_{10}$ selectivity from an industrial heavy reformate stream obtained with commercially available zeolite catalysts and composite zeolite catalyst particles synthesized in accordance with one or more embodiments of the present disclosure.
Figure 28:
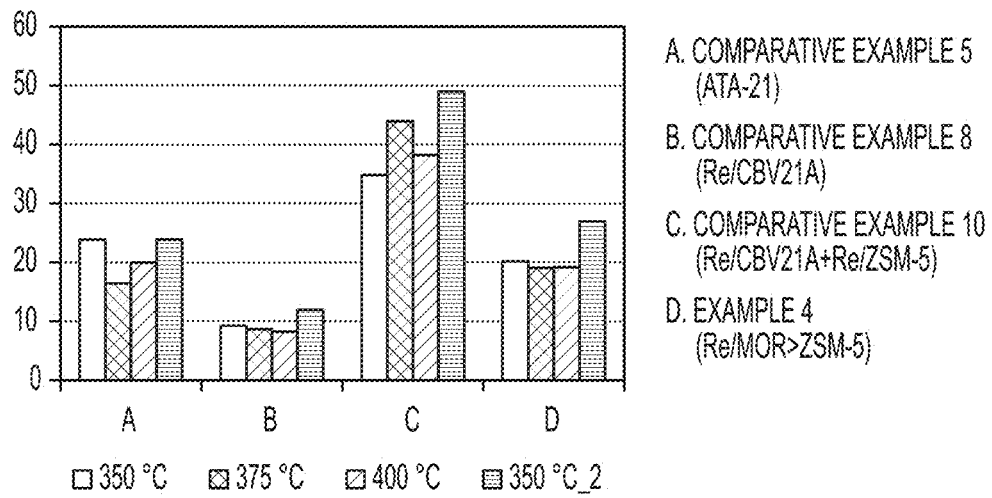
FIG. 28 is a graph of $A_{10+}$ selectivity from an industrial heavy reformate stream obtained with commercially available zeolite catalysts and composite zeolite catalyst particles synthesized in accordance with one or more embodiments of the present disclosure.
Figure 29:
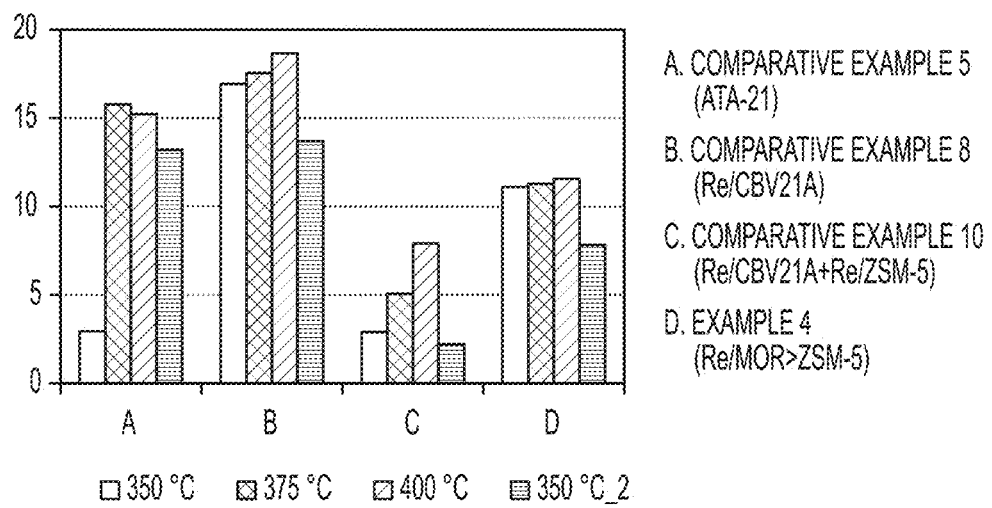
FIG. 29 is a graph of light hydrocarbon selectivity from an industrial heavy reformate stream obtained with commercially available zeolite catalysts and composite zeolite catalyst particles synthesized in accordance with one or more embodiments of the present disclosure.
Figure 30:
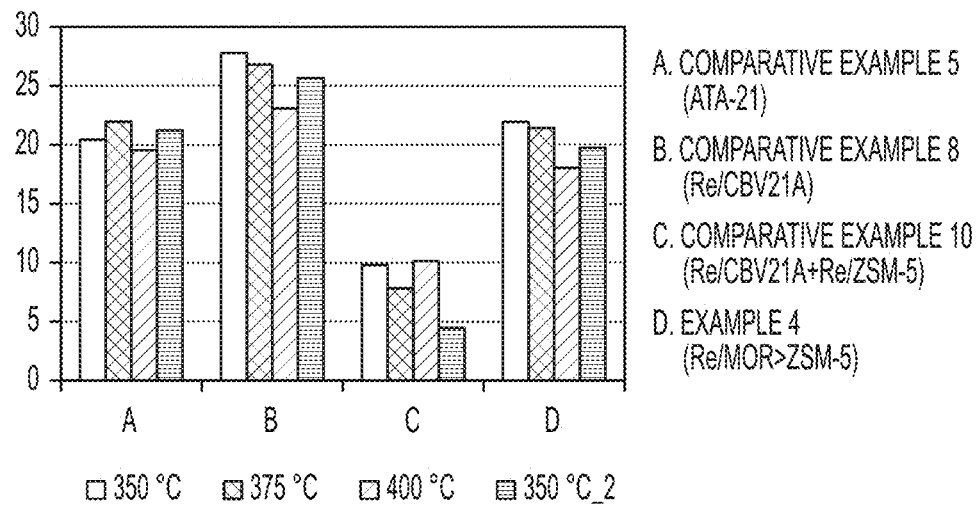
FIG. 30 is a graph of toluene selectivity from of an industrial heavy reformate stream obtained with commercially available zeolite catalysts and composite zeolite catalyst particles synthesized in accordance with one or more embodiments of the present disclosure.
Figure 31:
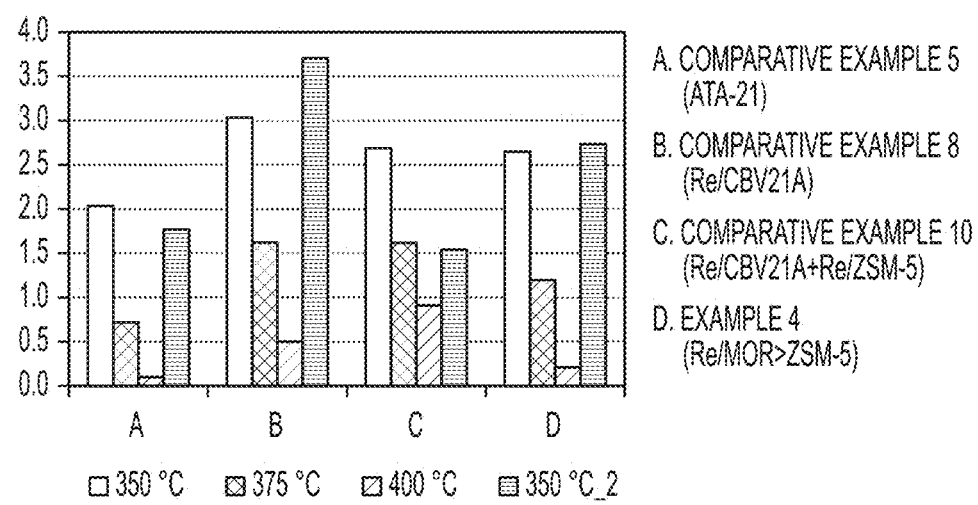
FIG. 31 is a graph of ethylbenzene selectivity from an industrial heavy reformate stream obtained with commercially available zeolite catalysts and composite zeolite catalyst particles synthesized in accordance with one or more embodiments of the present disclosure.
Figure 32:
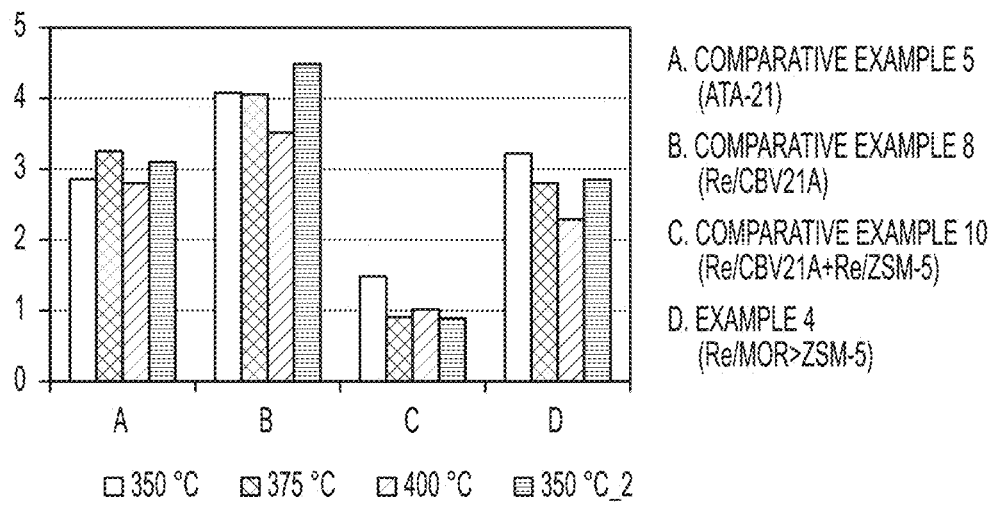
FIG. 32 is a graph of benzene selectivity from an industrial heavy reformate stream obtained with commercially available zeolite catalysts and composite zeolite catalyst particles synthesized in accordance with one or more embodiments of the present disclosure.

With reference to FIGS. 16, 17 and 18, the TMB conversion (transalkylation), MEB conversion (dealkylation), and overall conversion (MEB+TMB) are respectively illustrated for each of Example 4, Comparative Example 5. Comparative Example 8, and Comparative Example 10. It is noted that Example 4 (Re/Mordenite>ZSM-5) indicated lower overall conversion than the Comparative Examples which is attributed to the lower TMB conversion activity. However, the lower overall conversion is offset by the higher xylene production and reduced $A_{10+}$ formation. The individual TMB conversion percentages and MEB conversion percentages are provided in Table 7. It is also noted that larger ratios of the ZSM-5 component provides higher MEB conversion because ZSM-5 favors the dealkylation reaction while larger Mordenite content results in catalysts more active for the TMB conversion.

TABLE 7

MEB, TMB, and Overall Conversion

| Catalyst | Temperature | MEB Conversion (%) | TMB Conversion (%) | Overall Conversion (%) |
|---|---|---|---|---|
| Comparative | 350° C. | 70.53 | 22.22 | 34.18 |
| Example 5 | 375° C. | 94.12 | 37.64 | 51.62 |
| (ATA-21) | 400° C. | 98.72 | 34.62 | 50.48 |
| | 350° C. (Return) | 74.76 | 27.44 | 39.15 |
| Comparative | 350° C. | 40.81 | 23.08 | 27.76 |
| Example 8 | 375° C. | 61.07 | 31.92 | 39.62 |
| (Re/CBV21A) | 400° C. | 77.44 | 42.55 | 51.77 |
| | 350° C. (Return) | 35.84 | 15.89 | 21.16 |
| Comparative | 350° C. | 69.80 | 26.67 | 38.25 |
| Example 10 | 375° C. | 84.43 | 32.95 | 46.77 |
| (Re/CBV21A + | 400° C. | 94.92 | 42.03 | 56.23 |
| Re/CBV3024E) | 350° C. (Return) | 49.57 | 18.77 | 27.04 |
| Example 4 | 350° C. | 62.95 | 4.30 | 20.48 |
| (Re/MOR > | 375° C. | 87.45 | 11.17 | 32.23 |
| ZSM-5) | 400° C. | 97.26 | 21.83 | 42.65 |
| | 350° C. (Return) | 54.89 | 2.00 | 12.31 |

With reference to FIGS. 19, 20, 21, 22, 23, 24, and 25, the xylenes yield, $A_{10}$ yield, $A_{10+}$ yield, light hydrocarbon yield, toluene yield, ethylbenzene yield, and benzene yield are respectively illustrated for each of the 4 sample types. It is noted that Example 4 (Re/MOR>ZSM-5) favors the xylenes production as compared to Comparative Example 8 (Re/

CBV21A) and Comparative Example 10 (Re/CBV21A+Re/CBV3024E) and is comparable to Comparative Example 5 (ATA-21) (commercially available physical mixture of Mordenite and ZSM-5). Additionally, Example 4 (Re/MOR>ZSM-5) presents less undesirable $A_{10+}$ fraction. The numerical values of the yield as a wt. % for each species utilizing each catalyst is provided in Table 8. This improvement in xylenes production and concurrent reduction in $A_{10+}$ fraction illustrates the benefit of synthesis according to the methods of the present disclosure where the Mordenite and ZSM-5 are in intimate contact opposed to physically mixing Mordenite and ZSM-5 after formation. An additional advantage is that the active multizeolite phase, containing ZSM-5 and Mordenite zeolites, is obtained in a single step one-pot synthesis, thereby reducing production complexity.

Figure 34:
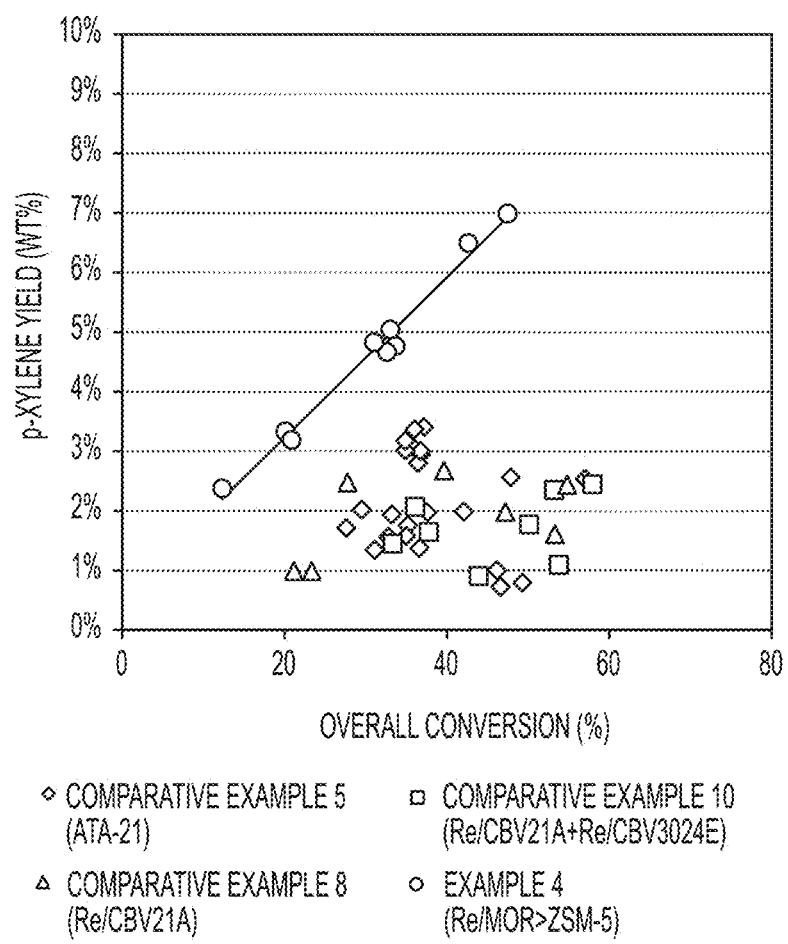
FIG. 34 is a graph of p-xylenes yield as a function of overall MEB and TMB conversion from an industrial heavy reformate stream obtained with commercially available zeolite catalysts and composite zeolite catalyst particles synthesized in accordance with one or more embodiments of the present disclosure.

(Re/MOR>ZSM-5) as illustrated in FIG. 34. p-Xylene is the most valuable of the xylene isomers with the highest industrial demand. It is a raw material in the large scale synthesis of terephthalic acid for making polymers and as such a higher selectivity toward p-xylene is desirable. The higher selectivity toward xylenes and more specifically p-xylene allows for a lower overall conversion while maintaining a higher xylene yield and more specifically p-xylene yield.

Example 4 (Re/MOR>ZSM-5), although less active than the commercial ATA-21 (Comparative Example 5), provides higher xylenes yield than ATA-21. This is believed to result because Example 4 is more selective to the desired xylenes than the commercial reference. Higher selectivity is beneficial from the point of view of separation and generation of undesired by-products. Additionally, within the xylenes

TABLE 8

Product Yields

| Catalyst | Temperature | Xylenes Yield (wt. %) | $A_{10}$ Yield (wt. %) | $A_{10+}$ Yield (wt. %) | Light HC Yield (wt. %) | Toluene Yield (wt. %) | Ethylbenzene Yield (wt. %) | Benzene Yield (wt. %) |
|---|---|---|---|---|---|---|---|---|
| Comparative Example 5 (ATA-21) | 350° C. | 15.60 | 3.94 | 11.91 | 2.95 | 10.22 | 1.02 | 1.43 |
|  | 375° C. | 23.28 | 1.55 | 9.73 | 9.35 | 13.02 | 0.43 | 1.93 |
|  | 400° C. | 24.32 | 2.72 | 12.56 | 9.62 | 12.34 | 0.06 | 1.77 |
|  | 350° C. (Return) | 15.08 | 3.35 | 11.94 | 6.61 | 10.63 | 0.88 | 1.55 |
| Comparative Example 8 (Re/CBV21A) | 350° C. | 12.69 | 8.01 | 15.17 | 1.26 | 4.27 | 1.17 | 0.65 |
|  | 375° C. | 14.02 | 7.38 | 23.22 | 2.68 | 4.13 | 0.85 | 0.48 |
|  | 400° C. | 20.71 | 5.29 | 23.87 | 4.93 | 6.31 | 0.57 | 0.63 |
|  | 350° C. (Return) | 6.74 | 8.92 | 18.81 | 0.85 | 1.72 | 0.59 | 0.34 |
| Comparative Example 10 (Re/CBV21A + Re/CBV3024E) | 350° C. | 16.24 | 3.36 | 4.66 | 8.63 | 14.05 | 1.52 | 2.06 |
|  | 375° C. | 20.84 | 2.80 | 4.94 | 10.09 | 15.42 | 0.93 | 2.33 |
|  | 400° C. | 28.35 | 1.48 | 5.31 | 12.15 | 15.04 | 0.32 | 2.29 |
|  | 350° C. (Return) | 12.32 | 4.40 | 4.93 | 5.72 | 10.69 | 1.54 | 1.87 |
| Example 4 (Re/MOR > ZSM-5) | 350° C. | 13.97 | 3.32 | 8.55 | 4.72 | 9.31 | 1.12 | 1.37 |
|  | 375° C. | 20.79 | 1.63 | 9.72 | 5.74 | 10.91 | 0.61 | 1.43 |
|  | 400° C. | 27.85 | 0.48 | 11.22 | 6.76 | 10.55 | 0.12 | 1.34 |
|  | 350° C. (Return) | 10.31 | 4.17 | 9.81 | 2.85 | 7.19 | 1.00 | 1.04 |

With reference to FIGS. 26, 27, 28, 29, 30, 31, and 32, the xylenes selectivity, $A_{10}$ selectivity, $A_{10+}$ selectivity, light hydrocarbon selectivity, toluene selectivity, ethylbenenze selectivity, and benzene selectivity are respectively illustrated for each of the 4 sample types. It is noted that Example 4 is significantly more selective to xylenes as compared to Comparative Example 8 (Re/CBV21A), Comparative Example 10 (Re/CBV21A+Re/CBV3024E) and even Comparative Example 5 (ATA-21) (commercially available physical mixture of Mordenite and ZSM-5).

The yield to a certain product is the amount produced as referred to the reactants fed. For example, kilograms (kg) xylenes/kg feed×100 provides the yield of xylenes. Similarly, the selectivity to a certain compound is its proportion within the total products obtained. For example, kg xylenes/kg products×100 provides the selectivity toward xylenes. A greater yield to a desired product is desirable as more of the desired product is produced. Additionally, a greater selectivity to a desired product is also desirable at a comparable conversion or yield as this results in lesser yields of unwanted by-products.

Figure 33:
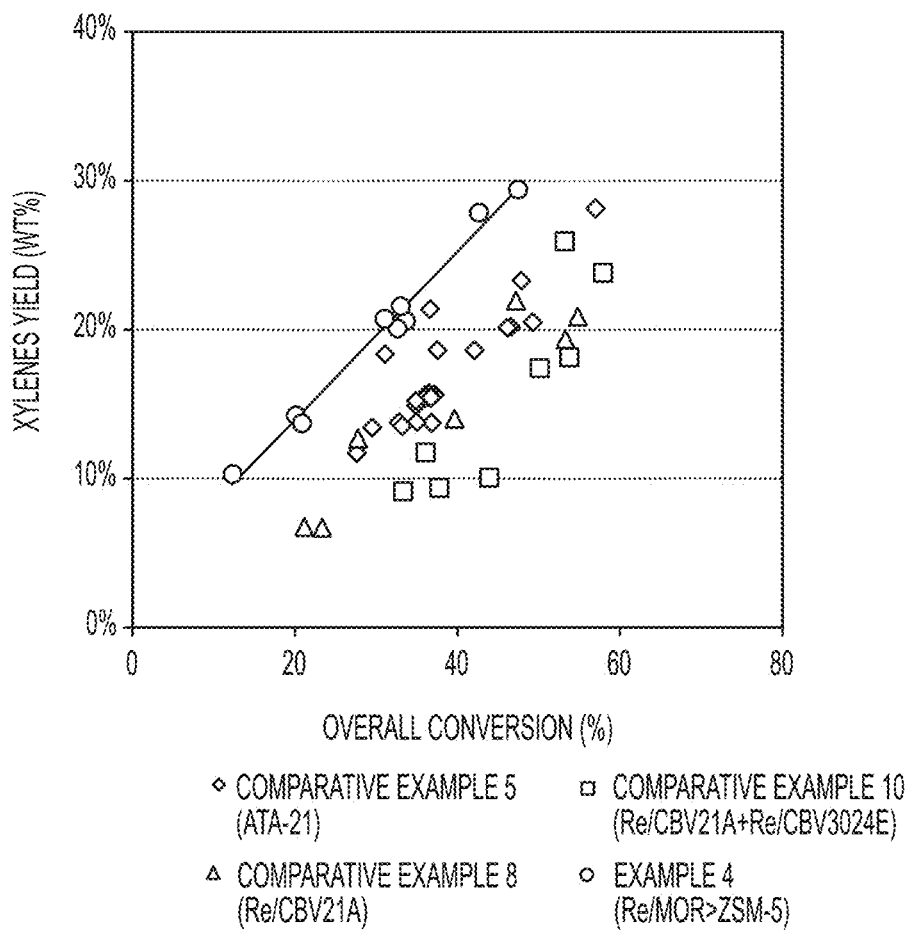
FIG. 33 is a graph of xylenes yield as a function of overall MEB and TMB conversion from an industrial heavy reformate stream obtained with commercially available zeolite catalysts and composite zeolite catalyst particles synthesized in accordance with one or more embodiments of the present disclosure.

The enhanced xylenes yield is further illustrated in FIG. 33. Example 4 (Re/MOR>ZSM-5) provides a marked increase in xylene yield for each progressively larger overall conversion when compared to the other 4 samples. Further, the selectivity to p-xylene is improved with Example 4 fraction, Example 4 is more selective to p-xylene, the most valuable isomer. Thus, high xylenes and p-xylene selectivity is a benefit provided by embodiments of this disclosure.

It should be understood that the various aspects of the composite zeolite catalyst, the method of making the same, the method of making xylene using the same, and a system for making xylene using the same are described and such aspects may be utilized in conjunction with various other aspects.

In a first aspect, the disclosure provides a method of forming composite zeolite catalyst particles. The method comprises combining NaOH, a silicon source, an organic structure directing agent, water and an aluminum source to form a catalyst gel, where the organic structure directing agent comprises a polyquaternary ammonium compound in accordance with:

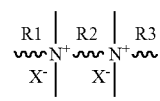

where, X is a hydroxide group or a halogen selected from Cl, Br, I, or combinations thereof; R1 is a substituted or an unsubstituted $C_{8-22}$ alkyl group; R2 is a substituted or an unsubstituted $C_{3-6}$ alkyl group; and R3 is a substituted or an unsubstituted $C_{1-8}$ alkyl group or an alkenyl group. The method further comprises stirring the catalyst gel for homogenization and heating the catalyst gel to form the composite zeolite catalyst particles, where the composite zeolite catalyst particle comprises both Mordenite and ZSM-5 zeolites and is characterized by having an intergrowth region comprising a mixture of both Mordenite crystals and ZSM-5 crystals.

In a second aspect, the disclosure provides the method of the first aspect in which the silicon source comprises a silica gel, silicon oxide, silicon halide, tetraalkyl orthosilicate, silicic acid, fumed silica, sodium silicate, colloidal silica, or combinations thereof.

In a third aspect, the disclosure provides the method of the first aspect in which the silicon source is a silica gel and the silica gel is a 20 to 60 wt. % suspension of silica in water.

In a fourth aspect, the disclosure provides the method of any of the first through third aspect in which the polyquaternary ammonium compound is a diquaternary ammonium compound.

In a fifth aspect, the disclosure provides the method of the first aspect in which X is a halogen selected from Cl, Br, I, or combinations thereof, R1 is a substituted or an unsubstituted C18-22 alkyl group; R2 is a substituted or an unsubstituted C6 alkyl group; and R3 is a substituted or an unsubstituted C6-8 alkyl group or an alkenyl group.

In a sixth aspect, the disclosure provides the method of any of the first through fifth aspects in which the aluminum source comprises $NaAlO_2$.

In a seventh aspect, the disclosure provides the method of any of the first through sixth aspects in which the aluminum source, the silicon source, the organic structure directing agent, and the water are further combined with NaOH to form the catalyst gel.

In an eighth aspect, the disclosure provides the method of any of the first through seventh aspects in which the heating of the catalyst gel is conducted in a sealed vessel under autogenous pressure at a temperature from 130 to 180° C. with stirring and the heating is continued for 10 to 18 days.

In a ninth aspect, the disclosure provides the method of any of the first through eighth aspects in which the method further comprises impregnating the composite zeolite catalyst with 0.01 wt. % to 20 wt. % of one or more metals selected from the group consisting of molybdenum, chromium, platinum, nickel, tungsten, palladium, ruthenium, gold, rhenium, rhodium, or combinations thereof and their respective oxides to yield impregnated composite zeolite catalyst particles.

In a tenth aspect, the disclosure provides a composite zeolite catalyst. The composite zeolite catalyst comprises ZSM-5 and Mordenite within a single catalyst particle. The composite zeolite catalyst has an intergrowth region with a mixture of Mordenite crystals and ZSM-5 crystals, the intergrowth of ZSM-5 and Mordenite characterized by an XRD curve having signature peaks at 6.6±0.2, 7.9±0.2, 8.8±0.2, 9.8±0.2, 13.6±0.2, 19.7±0.2, 22.5±0.2, 23.1±0.2, 23.9±0.2, 25.8±0.2, 26.4±0.2, 27.7±0.2. The composite zeolite catalyst has a Mordenite to ZSM-5 molar ratio from 3:1 to 2:3, the molar ratio of silicon to aluminum (Si/Al) in the zeolite composite catalyst is from 5:1 to 30:1, and the composite zeolite catalyst further comprises 0.01 wt. % to 20 wt. % of one or more metals selected from the group consisting of platinum, nickel, tungsten, palladium, ruthenium, gold, rhenium, rhodium, or combinations thereof to yield impregnated zeolite catalyst.

In an eleventh aspect, the disclosure provides the composite zeolite catalyst of any of the tenth aspects in which the metal comprises rhenium.

In a twelfth aspect, the disclosure provides a method of making xylene. The method comprises feeding heavy reformate to a reactor, the reactor comprising a plurality of composite zeolite catalyst particles, where each composite zeolite catalyst particle comprises both ZSM-5 and Mordenite zeolites and has an intergrowth region with a mixture of both Mordenite crystals and ZSM-5 crystals. The method further comprises producing xylene by simultaneously performing transalkylation and dealkylation of the heavy reformate in the reactor. Each composite zeolite catalyst particle is able to simultaneously catalyze both the transalkylation and dealkylation reactions. The composite zeolite catalyst further comprises 0.01 wt. % to 20 wt. % of one or more metals selected from the group consisting of molybdenum, chromium, nickel, tungsten, ruthenium, gold, rhenium, rhodium, or combinations thereof.

In a thirteenth aspect, the disclosure provides the method of the twelfth aspect in which the heavy reformate comprises at least 15 wt. % methylethylbenzene (MEB) and at least 50 wt. % trimethylbenzene (TMB).

In a fourteenth aspect, the disclosure provides the method of the twelfth aspect in which the composite zeolite catalyst has a Mordenite to ZSM-5 molar ratio from 3:1 to 2:3.

In a fifteenth aspect, the disclosure provides the method of the twelfth aspect in which the molar ratio of silicon to aluminum (Si/Al) in the zeolite composite catalyst is from 5:1 to 30:1.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A method of forming composite zeolite catalyst particles, the method comprising: combining NaOH, a silicon source, an organic structure directing agent, water and an aluminum source to form a catalyst gel, where the organic structure directing agent comprises a polyquaternary ammonium compound in accordance with:

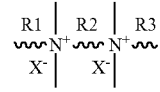

where,
X is a hydroxide group or a halogen selected from Cl, Br, I, or combinations thereof;
R1 is a substituted or an unsubstituted $C_{8-22}$ alkyl group;
R2 is a substituted or an unsubstituted $C_{3-6}$ alkyl group; and
R3 is a substituted or an unsubstituted $C_{1-8}$ alkyl group or an alkenyl group;
stirring the catalyst gel for homogenization; and heating the catalyst gel to form the composite zeolite catalyst particles, where the composite zeolite catalyst particle comprises both Mordenite and ZSM-5 zeolites and is characterized by having an intergrowth region comprising a mixture of both Mordenite crystals and ZSM-5 crystals.

2. The method of claim 1 where the silicon source comprises a silica gel, silicon oxide, silicon halide, tetraalkyl orthosilicate, silicic acid, fumed silica, sodium silicate, colloidal silica, or combinations thereof.

3. The method of claim 1 where the silicon source is a silica gel and the silica gel is a 20 to 60 wt. % suspension of silica in water.

4. The method of claim 1 where the polyquaternary ammonium compound is a diquaternary ammonium compound.

5. The method of claim 1 where,
X is a halogen selected from Cl, Br, I, or combinations thereof,
R1 is a substituted or an unsubstituted $C_{18-22}$ alkyl group;
R2 is a substituted or an unsubstituted $C_6$ alkyl group; and
R3 is a substituted or an unsubstituted $C_{6-8}$ alkyl group or an alkenyl group.

6. The method of claim 1 where the aluminum source comprises $NaAlO_2$.

7. The method of claim 1 where the aluminum source, the silicon source, the organic structure directing agent, and the water are further combined with NaOH to form the catalyst gel.

8. The method of claim 1 where the heating of the catalyst gel is conducted in a sealed vessel under autogenous pressure at a temperature from 130 to 180° C. with stirring and the heating is continued for 10 to 18 days.

9. The method of claim 1 where the method further comprises impregnating the composite zeolite catalyst with 0.01 wt. % to 20 wt. % of one or more metals selected from the group consisting of molybdenum, chromium, platinum, nickel, tungsten, palladium, ruthenium, gold, rhenium, rhodium, or combinations thereof to yield impregnated composite zeolite catalyst particles.

10. A composite zeolite catalyst,
the composite zeolite catalyst comprises ZSM-5 and Mordenite within a single catalyst particle,
where the composite zeolite catalyst has an intergrowth region with a mixture of Mordenite crystals and ZSM-5 crystals, the intergrowth of ZSM-5 and Mordenite characterized by an XRD curve having signature peaks at 6.6±0.2, 7.9±0.2, 8.8±0.2, 9.8±0.2, 13.6±0.2, 19.7±0.2, 22.5±0.2, 23.1±0.2, 23.9±0.2, 25.8±0.2, 26.4±0.2, 27.7±0.2 degrees, where
the composite zeolite catalyst has a Mordenite to ZSM-5 molar ratio from 3:1 to 2:3,
the molar ratio of silicon to aluminum (Si/Al) in the zeolite composite catalyst is from 5:1 to 30:1, and
the composite zeolite catalyst further comprises 0.01 wt. % to 20 wt. % of one or more metals selected from the group consisting of platinum, nickel, tungsten, palladium, ruthenium, gold, rhenium, rhodium, or combinations thereof to yield impregnated zeolite catalyst.

11. The composite zeolite catalyst of claim 10, where the metal comprises rhenium.

12. A method of making xylene, the method comprising:
feeding heavy reformate to a reactor, the reactor comprising a plurality of composite zeolite catalyst particles, where each composite zeolite catalyst particle comprises both ZSM-5 and Mordenite zeolites and has an intergrowth region with a mixture of both Mordenite crystals and ZSM-5 crystals; and
producing xylene by simultaneously performing transalkylation and dealkylation of the heavy reformate in the reactor, where each composite zeolite catalyst particle is able to simultaneously catalyze both the transalkylation and dealkylation reactions, where
the composite zeolite catalyst further comprises 0.01 wt. % to 20 wt. % of one or more metals selected from the group consisting of molybdenum, chromium, nickel, tungsten, ruthenium, gold, rhenium, rhodium, or combinations thereof.

13. The method of claim 12, where the heavy reformate comprises at least 15 wt. % methylethylbenzene (MEB) and at least 50 wt. % trimethylbenzene (TMB).

14. The method of claim 12, where the composite zeolite catalyst has a Mordenite to ZSM-5 molar ratio from 3:1 to 2:3.

15. The method of claim 12, where the molar ratio of silicon to aluminum (Si/Al) in the zeolite composite catalyst is from 5:1 to 30:1.

* * * * *

UNITED STATES PATENT AND TRADEMARK OFFICE
CERTIFICATE OF CORRECTION

Page 1 of 3

PATENT NO. : 10,723,631 B2
APPLICATION NO. : 16/299704
DATED : July 28, 2020
INVENTOR(S) : Raed Hasan Abudawoud et al.

It is certified that error appears in the above-identified patent and that said Letters Patent is hereby corrected as shown below:

On the Title Page

In page 2, Column 2, item (56), U.S. patent documents, cite no. 12, delete "Inui" and insert --Inui et al.--, therefor.

In the Specification

In Column 6, delete

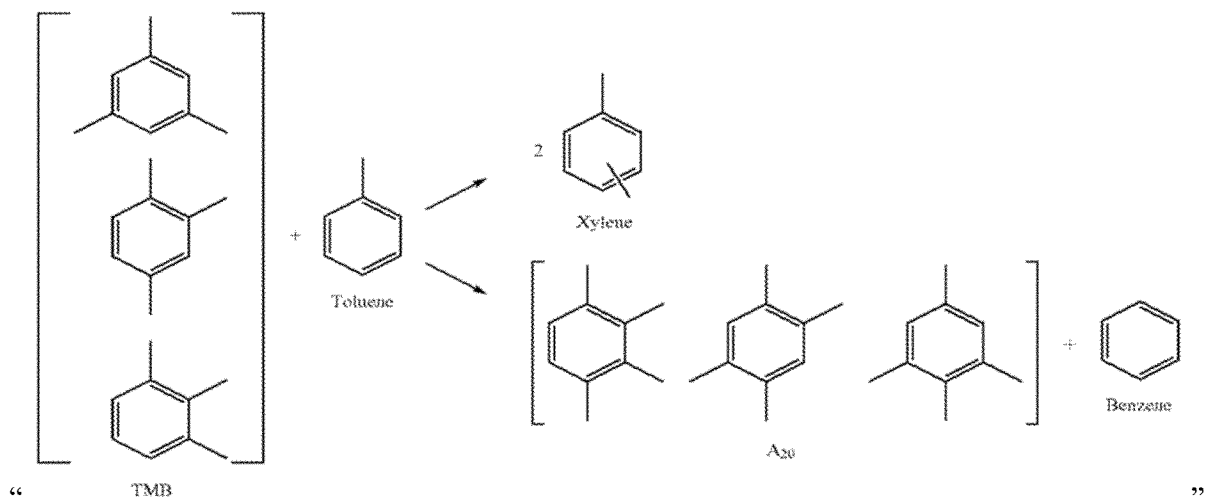

" TMB "

and insert

Signed and Sealed this
Seventeenth Day of November, 2020

Andrei Iancu
*Director of the United States Patent and Trademark Office*

-- 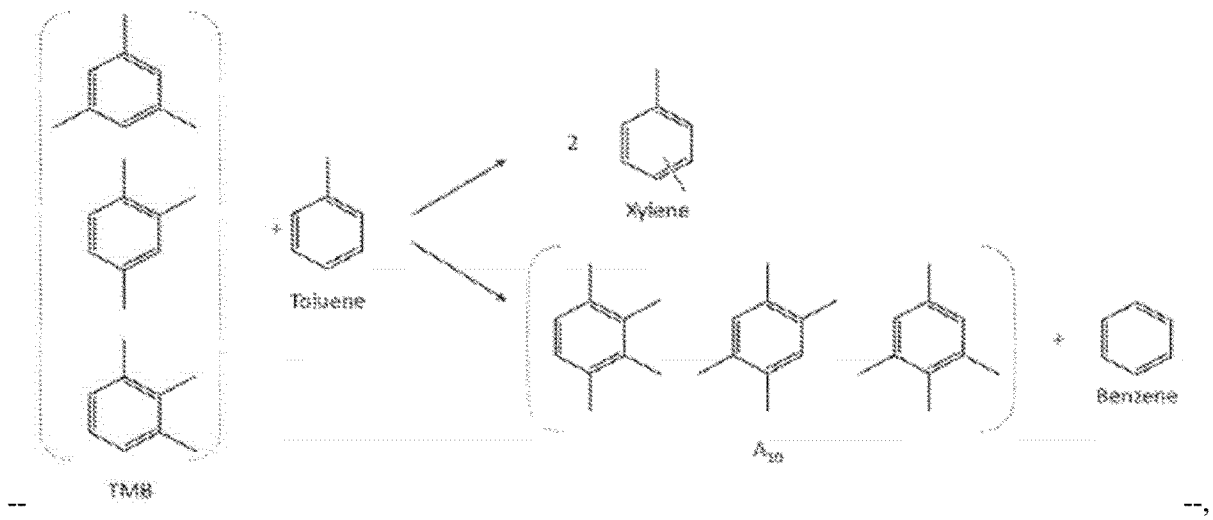 --, therefor.

In Column 9, Line(s) 35, before "R3", delete "m" and insert --in--, therefor.

In Column 9, Line(s) 42, after "C$_{22\text{-}6\text{-}6\text{-}6}$(OH)$_3$", delete "," and insert --:--, therefor.

In Column 11, Line(s) 15, after "14 h", delete "." and insert --,--, therefor.

In Column 12, Line(s) 53, delete "6.5" and insert --6:5--, therefor.

In Column 12, Line(s) 54, delete "26" and insert --2:6--, therefor.

In Column 16, Line(s) 46, delete "physio-chemical" and insert --physico-chemical--, therefor.

In Column 18, Line(s) 13, delete "150 C" and insert --150° C--, therefor.

In Column 18, Line(s) 14, after "3600", delete "cm-1" and insert --cm$^{-1}$--, therefor.

In Column 19, Line(s) 23, delete "8.5" and insert --8:5--, therefor.

In Column 20, Line(s) 13, after "(dealkylation)", delete "." and insert --,--, therefor.

In Column 20, Line(s) 45, after "yield", delete "." and insert --,--, therefor.

In Column 21, Line(s) 54, after "Example 5", delete "." and insert --,--, therefor.

In Column 22, Line(s) 24, after "Example 5", delete "." and insert --,--, therefor.

In Column 25, Line(s) 26, delete "C18-22" and insert --C$_{18\text{-}22}$--, therefor.

In Column 25, Line(s) 27, delete "C6" and insert --$C_6$--, therefor.

In Column 25, Line(s) 28, delete "C6-8" and insert --$C_{6-8}$--, therefor.